United States Patent
Barth et al.

(10) Patent No.: US 9,944,706 B2
(45) Date of Patent: Apr. 17, 2018

(54) IMMUNOPROTEASES

(71) Applicant: Fraunhofer-Gesellschaft zur Foerderung der angewandten Forschung e.V, Munich (DE)

(72) Inventors: Stefan Barth, Aachen (DE); Sonja Schiffer, Juechen (DE)

(73) Assignee: Fraunhofer-Gesellschaft zur Foerderung der angewandten Forschung e.V, Munich (DE)

( * ) Notice: Subject to any disclaimer, the term of this patent is extended or adjusted under 35 U.S.C. 154(b) by 0 days.

(21) Appl. No.: 14/440,947

(22) PCT Filed: Nov. 4, 2013

(86) PCT No.: PCT/EP2013/072888
§ 371 (c)(1),
(2) Date: May 6, 2015

(87) PCT Pub. No.: WO2014/072233
PCT Pub. Date: May 15, 2014

(65) Prior Publication Data
US 2015/0291693 A1    Oct. 15, 2015

(30) Foreign Application Priority Data
Nov. 7, 2012  (EP) .................... 12191711

(51) Int. Cl.
C12N 5/00     (2006.01)
C12N 15/00    (2006.01)
C07K 16/00    (2006.01)
C07K 16/28    (2006.01)
C12N 9/64     (2006.01)
C12N 9/76     (2006.01)

(52) U.S. Cl.
CPC ........ C07K 16/283 (2013.01); C07K 16/2863 (2013.01); C07K 16/2866 (2013.01); C07K 16/2878 (2013.01); C12N 9/6427 (2013.01); C12N 9/6467 (2013.01); C07K 2317/622 (2013.01); C07K 2317/73 (2013.01); C07K 2319/00 (2013.01); C07K 2319/50 (2013.01); C07K 2319/55 (2013.01)

(58) Field of Classification Search
None
See application file for complete search history.

(56) References Cited

U.S. PATENT DOCUMENTS

| | | | |
|---|---|---|---|
| 8,017,747 B2 * | 9/2011 | Caldas | A61K 48/0058 435/975 |
| 8,993,295 B2 * | 3/2015 | Seed | A61K 47/48561 435/188 |
| 2003/0086919 A1 | 5/2003 | Rosenblum et al. | |
| 2006/0263368 A1 * | 11/2006 | Rosenblum | A61K 41/0038 424/155.1 |
| 2009/0081185 A1 * | 3/2009 | Barth | A61K 39/35 424/94.64 |
| 2014/0356347 A1 * | 12/2014 | Barth | C12N 9/6467 424/94.64 |

FOREIGN PATENT DOCUMENTS

WO    2008011157 A2    1/2008
WO    2009014650 A2    1/2009

OTHER PUBLICATIONS

Bowie et al, 1990, Science 247:1306-1310.*
Wells, 1990, Biochemistry 29:8509-8517.*
Ngo et al., 1994, The Protein Folding Problem and Tertiary Structure Prediction, Merz et al., eds, Birkhauser, Boston, pp. 433-506.*
Wang et al 2001. J. Biol Chem. 276:49213-49220.*
Paul, Fundamental Immunology, 3rd Edition, 1993, pp. 292-295, under the heading "Fv Structure and Diversity in Three Dimensions".*
Rudikoff et al Proc. Natl. Acad. Sci.USA, 79(6):1979-1983, Mar. 1982.*
Colman P. M. Research in Immunology, 145:33-36, 1994.*
Piatesi et al ChemBio Chem 5: 460-466, 2004.*
Stancovski et al. Proceedings of the National Academy of Science USA 88: 8691-8695, 1991.*
Bremer et al. 2005. J. Biol Chem. 280:10025-10033.*
PCT/EP2013/072888 International Search Report mailed 28 Feb. 2014.

* cited by examiner

Primary Examiner — Shulamith H Shafer
(74) Attorney, Agent, or Firm — Wagenknecht IP Law Group PC

(57) ABSTRACT

The technology provided herein relates to novel immunoproteases suitable to induce apotosis in selected diseased target cells, comprising the serine protease granzyme M, and methods for using such cytolytic fusion proteins for the treatment of various diseases, in particular for the treatment of cancer.

19 Claims, 22 Drawing Sheets

Examples for schematic structure for hCFP on nucleotide level including granzyme M pMS-L-EGm-Ki4(scFv)-IV pMS-L-EGm-H22(scFv)-IV pMS-L-EGm-425(scFv)-IV pMS-L-EGm-RFT5(scFv)-IV

A)

M – Prestained Protein Marker
1 – Gm – H22(scFv)

B)

a Gm-H22
b Gm-H22 + PI9
c PI9

A)

M – Prestained Protein Marker
1 – Gm – Ki4(scFv)

B)

a) Gm-Ki4
b) PI9
c) Gm-Ki4 + PI9

A)

M – Prestained Protein Marker
1 – Gm – 425(scFv)

B)

a) PI9
b) Gm-425(scFv)
c) Gm-425(scFv) + PI9

M – Prestained Protein Marker
1 – Gm – RFT5(scFv)

M – Prestained Protein Marker
1 – Gm – RFT5(scFv)

Wild type Granzyme M

A) Nucleic acid sequence of wild type human granzyme M (SEQ ID NO: 1)

```
atcatcgggg gccgggaggt gatccccac tcgcgccgt acatggcctc actgcagaga
aatggctccc acctgtgcgg gggtgtcctg gtgcacccaa agtgggtgct gacggctgcc
cactgcctgg cccagcggat ggcccagctg aggctggtgc tggggctcca caccctggac
agccccggtc tcaccttcca catcaaggca gccatccagc accctcgcta caagcccgtc
cctgccctgg agaacgacct cgcgctgctt cagctggacg ggaaagtgaa gcccagccgg
accatccggc cgttggccct gcccagtaag cgccaggtgg tggcagcagg gactcggtgc
agcatggccg gctggggct gacccaccag ggcgggcgcc tgtcccgggt gctgcgggag
ctggacctcc aagtgctgga cacccgcatg tgtaacaaca gccgcttctg gaacggcagc
ctctccccca gcatggtctg cctggcggcc gactccaagg accaggctcc ctgcaagggt
gactcgggcg ggcccctggt gtgtggcaaa ggccgggtgt tggccggagt cctgtccttc
agctccaggg tctgcactga catcttcaag cctcccgtgg ccaccgctgt ggcgccttac
gtgtcctgga tcaggaaggt caccggccga tcggcc
```

B) Amino acid sequence of human wild type granzyme M (SEQ ID NO: 2)

```
IIGGREVIPH SRPYMASLQR NGSHLCGGVL VHPKWVLTAA HCLAQRMAQL RLVLGLHTLD
SPGLTFHIKA AIQHPRYKPV PALENDLALL QLDGKVKPSR TIRPLALPSK RQVVAAGTRC
SMAGWGLTHQ GGRLSRVLRE LDLQVLDTRM CNNSRFWNGS LSPSMVCLAA DSKDQAPCKG
DSGGPLVCGK GRVLAGVLSF SSRVCTDIFK PPVATAVAPY VSWIRKVTGR SA
```

FIGURE 19

Granzyme M variant Gm-H22(scFv)

A) Nucleic acid sequences of Gm-H22(scFv) (SEQ ID NO: 3)

```
atcatcgggg gccgggaggt gatccccac tcgcgcccgt acatggcctc actgcagaga
aatggctccc acctgtgcgg gggtgtcctg gtgcacccaa agtgggtgct gacggctgcc
cactgcctgg cccagcggat ggcccagctg aggctggtgc tggggctcca caccctggac
agccccggtc tccaccttcca catcaaggca gccatccagc ccctcgcta caagcccgtc
cctgccctgg agaacgacct cgcgctgctt cagctggacg ggaaagtgaa gcccagccgg
accatccggc cgttggccct gcccagtaag cgccaggtgg tggcagcagg gactcggtgc
agcatggccg gctgggggct gacccaccag ggcgggcgcc tgtcccgggt gctgcgggag
ctggacctcc aagtgctgga caccgcatg tgtaacaaca gccgcttctg gaacggcagc
ctctccccca gcatggtctg cctggcggcc gactccaagg accaggctcc ctgcaagggt
gactcgggcg ggcccctggt gtgtggcaaa gccgggtgt tggccggagt cctgtccttc
agctccaggg tctgcactga catcttcaag cctcccgtgg ccaccgctgt ggcgccttac
gtgtcctgga tcaggaaggt caccggccga tcggccgctg agcacgaagg tgacgcggcc
cagccggcca tgccccaggt gcagctggtg gagagcggtg gaggtgttgt gcaacctggc
cggtccctgc gcctgtcctg ctcctcgtct ggcttcattt tcagtgacaa ttacatgtat
tgggtgagac aggcacctgg aaaaggtctt gagtgggttg caaccattag tgatggtggt
agttacacct actatccaga cagtgtgaag ggaagattta caatatcgag agacaacagc
aagaacacat tgttcctgca aatggacagc ctgagacccg aagacaccgg ggtctatttt
tgtgcaagag gctactatag gtacgagggg gctatggact actggggcca agggaccccg
gtcaccgtga gctcaggagg tggcggctcc ggaggtggag gcagcggagg ggcggatcc
gacatccagc tgacccagag cccaagcagc ctgagcgcca gcgtgggtga cagagtgacc
atcacctgta agtccagtca agtgttta tacagttcaa atcagaagaa ctacttggcc
tggtaccagc agaagccagg taaggctcca aagctgctga tctactgggc atccactagg
gaatctggtg tgccaagcag attcagcggt agcggtagcg gtaccgactt caccttcacc
atcagcagcc tccagccaga ggacatcgcc acctactact gccatcaata cctctcctcg
tggacgttcg gccaagggac caagctggag atcaaa
```

B) Amino acid sequences of Gm-H22(scFv) (SEQ ID NO: 4)

```
IIGGREVIPH SRPYMASLQR NGSHLCGGVL VHPKWVLTAA HCLAQRMAQL RLVLGLHTLD
SPGLTFHIKA AIQHPRYKPV PALENDLALL QLDGKVKPSR TIRPLALPSK RQVVAAGTRC
SMAGWGLTHQ GGRLSRVLRE LDLQVLDTRM CNNSRFWNGS LSPSMVCLAA DSKDQAPCKG
DSGGPLVCGK GRVLAGVLSF SSRVCTDIFK PPVATAVAPY VSWIRKVTGR SAAEHEGDAA
QPAMAQVQLV ESGGGVVQPG RSLRLSCSSS GFIFSDNYMY WVRQAPGKGL EWVATISDGG
SYTYYPDSVK GRFTISRDNS KNTLFLQMDS LRPEDTGVYF CARGYYRYEG AMDYWGQGTP
VTVSSGGGGS GGGGSGGGGS DIQLTQSPSS LSASVGDRVT ITCKSSQSVL YSSNQKNYLA
WYQQKPGKAP KLLIYWASTR ESGVPSRFSG SGSGTDFTFT ISSLQPEDIA TYYCHQYLSS
WTFGQGTKLE IK
```

FIGURE 20

Granzyme M variant Gm-Ki4(scFv)

A) Nucleic acid sequences of Gm-Ki4(scFv) (SEQ ID NO: 5)

```
atcatcgggg gccgggaggt gatcccccac tcgcgcccgt acatggcctc actgcagaga
aatggctccc acctgtgcgg gggtgtcctg gtgcacccaa agtgggtgct gacggctgcc
cactgcctgg cccagcggat ggcccagctg aggctggtgc tggggctcca caccctggac
agccccggtc tcaccttcca catcaaggca gccatccagc accctcgcta caagcccgtc
cctgccctgg agaacgacct cgcgctgctt cagctggacg ggaaagtgaa gcccagccgg
accatccggc cgttggccct gcccagtaag cgccaggtgg tggcagcagg gactcggtgc
agcatggccg gctgggggct gacccaccag ggcgggcgcc tgtcccgggt gctgcgggag
ctggacctcc aagtgctgga cacccgcatg tgtaacaaca gccgcttctg gaacggcagc
ctctccccca gcatggtctg cctggcggcc gactccaagg accaggctcc ctgcaagggt
gactcgggcg ggcccctggt gtgtggcaaa ggccgggtgt tggccggagt cctgtccttc
agctccaggg tctgcactga catcttcaag cctcccgtgg ccaccgctgt ggcgccttac
gtgtcctgga tcaggaaggt caccggccga tcggccgctg agcacgaagg tgacgcggcc
cagccggcca tggcccaggt caagctgcag gagtcaggga ctgaactggc aaagcctggg
gccgcagtga agatgtcctg caaggcttct ggctacacct ttactgacta ctggatgcac
tgggttaaac agaggcctgg acagggtctg gaatggattg gatacattaa tcctaacact
gcttatactg actacaatca gaaattcaag gacaaggcca cattgactgc agacaaatcc
tccagcacag cctacatgca actgcgcagc ctgacctctg aggattctgc agtctattac
tgtgcaaaaa agacaactca gactacgtgg gggtttcctt tttggggcca agggaccacg
gtcaccgtct cctcaggtgg aggcggttca ggcggaggtg gctctggcgg tggcggatcg
gacattgtgc tgacccagtc tccaaaatcc atggccatgt cagtcggaga gagggtcacc
ttgagctgca aggccagtga gaatgtggat tctttttgttt cctggtatca acagaaacca
ggccagtctc ctaaactgct gatatacggg gcctccaacc ggtacactgg ggtccccgat
cgcttcgcag gcagtggatc tggaagagat ttcactctga ccatcagcag tgtgcaggct
gaagaccttg cagattatca ctgtggacag aattacaggt atccgctcac gttcggtgct
ggcaccaagc tggaaatcaa acgg
```

B) Amino acid sequences of Gm-Ki4(scFv) (SEQ ID NO: 6)

```
IIGGREVIPH SRPYMASLQR NGSHLCGGVL VHPKWVLTAA HCLAQRMAQL RLVLGLHTLD
SPGLTFHIKA AIQHPRYKPV PALENDLALL QLDGKVKPSR TIRPLALPSK RQVVAAGTRC
SMAGWGLTHQ GGRLSRVLRE LDLQVLDTRM CNNSRFWNGS LSPSMVCLAA DSKDQAPCKG
DSGGPLVCGK GRVLAGVLSF SSRVCTDIFK PPVATAVAPY VSWIRKVTGR SAAEHGDAA
QPAMAQVKLQ ESGTELAKPG AAVKMSCKAS GYTFTDYWMH WVKQRPGQGL EWIGYINPNT
AYTDYNQKFK DKATLTADKS SSTAYMQLRS LTSEDSAVYY CAKKTTQTTW GFPFWGQGTT
VTVSSGGGGS GGGGSGGGGS DIVLTQSPKS MAMSVGERVT LSCKASENVD SFVSWYQQKP
GQSPKLLIYG ASNRYTGVPD RFAGSGSGRD FTLTISSVQA EDLADYHCGQ NYRYPLTFGA
GTKLEIKR
```

FIGURE 21

Granzyme M variant Gm-425(scFv)

A) Nucleic acid sequences of Gm-425(scFv) (SEQ ID NO: 7)

```
atcatcgggg gccgggaggt gatcccccac tcgcgcccgt acatggcctc actgcagaga
aatggctccc acctgtgcgg gggtgtcctg gtgcacccaa agtgggtgct gacggctgcc
cactgcctgg cccagcggat ggcccagctg aggctggtgc tgggctcca caccctggac
agccccggtc tcaccttcca catcaaggca gccatccagc accctcgcta caagcccgtc
cctgccctgg agaacgacct cgcgctgctt cagctggacg ggaaagtgaa gcccagccgg
accatccggc cgttggccct gccagtaag cgccaggtgg tggcagcagg gactcggtgc
agcatggccg gctgggggct gacccaccag ggcgggcgcc tgtcccgggt gctgcgggag
ctggacctcc aagtgctgga cacccgcatg tgtaacaaca gccgcttctg gaacggcagc
ctctccccca gcatggtctg cctggcggcc gactccaagg accaggctcc ctgcaagggt
gactcgggcg ggcccctggt gtgtggcaaa ggccgggtgt tggccggagt cctgtccttc
agctccaggg tctgcactga catcttcaag cctcccgtgg ccaccgctgt ggcgccttac
gtgtcctgga tcaggaaggt caccggccga tcggccgctg agcacgaagg tgacgcggcc
cagccggcca tggcgcaggt gcaactgcag cagtctgggg ctgaactggt gaagcctggg
gcttcagtga agttgtcctg caaggcttcc ggctacacct tcaccagcca ctggatgcac
tgggtgaagc agagggctgg acaaggcctt gagtggatcg gagagtttaa tcccagcaac
ggccgtacta actacaatga gaaattcaag agcaaggcca cactgactgt agacaaatcc
tccagcacag cctacatgca actcagcagc ctgacatctg aggactctgc ggtctattac
tgtgccagtc gggactatga ttacgacgga cggtactttg actactgggg ccaagggacc
acggtcaccg tctcctcagg tggcggtggc tcgggcggtg gtgggtcggg tggcggcgga
tctgacatcg agctcaccca gtctccagca atcatgtctg catctccagg ggagaaggtc
actatgacct gcagtgccag ctcaagtgta acttacatgt attggtacca gcagaagcca
ggatcctccc ccagactcct gatttatgac acatccaacc tggcttctgg agtccctgtt
cgtttcagtg gcagtgggtc tgggacctct tactctctca caatcagccg aatggaggct
gaagatgctg ccacttatta ctgccagcag tggagtagtc acatattcac gttcggctcg
gggacagaac tcgagatcaa acgg
```

B) Amino acid sequences of Gm-425(scFv) (SEQ ID NO: 8)

```
IIGGREVIPH SRPYMASLQR NGSHLCGGVL VHPKWVLTAA HCLAQRMAQL RLVLGLHTLD
SPGLTFHIKA AIQHPRYKPV PALENDLALL QLDGKVKPSR TIRPLALPSK RQVVAAGTRC
SMAGWGLTHQ GGRLSRVLRE LDLQVLDTRM CNNSRFWNGS LSPSMVCLAA DSKDQAPCKG
DSGGPLVCGK GRVLAGVLSF SSRVCTDIFK PPVATAVAPY VSWIRKVTGR SAAEHEGDAA
QPAMAQVQLQ QSGAELVKPG ASVKLSCKAS GYTFTSHWMH WVKQRAGQGL EWIGEFNPSN
GRTNYNEKFK SKATLTVDKS SSTAYMQLSS LTSEDSAVYY CASRDYDYDG RYFDYWGQGT
TVTVSSGGGG SGGGGSGGGG SDIELTQSPA IMSASPGEKV TMTCSASSSV TYMYWYQQKP
GSSPRLLIYD TSNLASGVPV RFSGSGSGTS YSLTISRMEA EDAATYYCQQ WSSHIFTFGS
GTELEIKR
```

FIGURE 22

Granzyme M variant Gm-RFT5(scFv)

A) Nucleic acid sequences of Gm-RFT5(scFv) (SEQ ID NO: 9)

```
atcatcgggg gccgggaggt gatcccccac tcgcgcccgt acatggcctc actgcagaga
aatggctccc acctgtgcgg gggtgtcctg gtgcacccaa agtgggtgct gacggctgcc
cactgcctgg cccagcggat ggcccagctg aggctggtgc tggggctcca caccctggac
agccccggtc tcaccttcca catcaaggca gccatccagc accctcgcta caagcccgtc
cctgccctgg agaacgacct cgcgctgctt cagctggacg ggaaagtgaa gcccagccgg
accatccggc cgttggccct gcccagtaag cgccaggtgg tgcagcagg gactcggtgc
agcatggccg gctgggggct gacccaccag ggcgggcgcc tgtcccgggt gctgcgggag
ctggacctcc aagtgctgga cacccgcatg tgtaacaaca gccgcttctg gaacggcagc
ctctccccca gcatggtctg cctggcggcc gactccaagg accaggctcc ctgcaagggt
gactcgggcg ggcccctggt gtgtggcaaa ggccgggtgt tggccggagt cctgtccttc
agctccaggg tctgcactga catcttcaag cctcccgtgg ccaccgctgt ggcgccttac
gtgtcctgga tcaggaaggt caccggccga tcggccgctg agcacgaagg tgacgcggcc
cagccggccc aggtgaagct ggaggagtca gggactgtgc tggcaaggcc tggggcttcc
gtgaagatgt cctgcaaggc ttctggctac aggtttacca actactggat gcactgggta
aaacagaggc ctggacaggg tctagaatgg attggtgtta tttatcctgg aaatagtgat
actagctaca accagaagtt caaggcaag gccaaactga ctgcagtcac atccgccagc
actgcctaca tggagctcag cagcctgaca aatgaggact ctgcggtcta ttactgtaca
agagaggag aaggctctga ctactggggc caagggacca cggtcaccgt ctcctcaggt
ggaggcggtt caggcggagg tggctctggc ggtggcggat cgcaaattgt tctcacccag
tctccagcaa ccatggctgc atctcccggg gagaagatca ctatcacctg cagtgccagc
tcaagtataa gttccaatta cttgcattgg tatcagcaga gccaggatt ctcccctaaa
ctcttgattt ataggacttc caatctggct tctggagtcc cagctcgctt cagtggcagt
gggtctggga cctcttactc tctcacaatt ggcaccatgg aggctgaaga tgttgccact
tactactgcc agcagggtag tagtataccg tacacgttcg gaggggggac caagctggag
ctcaaa
```

B) Amino acid sequences of Gm-RFT5(scFv) (SEQ ID NO: 10)

```
IIGGREVIPH SRPYMASLQR NGSHLCGGVL VHPKWVLTAA HCLAQRMAQL RLVLGLHTLD
SPGLTFHIKA AIQHPRYKPV PALENDLALL QLDGKVKPSR TIRPLALPSK RQVVAAGTRC
SMAGWGLTHQ GGRLSRVLRE LDLQVLDTRM CNNSRFWNGS LSPSMVCLAA DSKDQAPCKG
DSGGPLVCGK GRVLAGVLSF SSRVCTDIFK PPVATAVAPY VSWIRKVTGR SAAEHEGDAA
QPAQVKLEES GTVLARPGAS VKMSCKASGY RFTNYWMHWV KQRPGQGLEW IGVIYPGNSD
TSYNQKFKGK AKLTAVTSAS TAYMELSSLT NEDSAVYYCT REGEGSDYWG QGTTVTVSSG
GGGSGGGGSG GGGSQIVLTQ SPATMAASPG EKITITCSAS SSISSNYLHW YQQKPGFSPK
LLIYRTSNLA SGVPARFSGS GSGTSYSLTI GTMEAEDVAT YYCQQGSSIP YTFGGGTKLE
LKAAAGP
```

IMMUNOPROTEASES

REFERENCE TO SEQUENCE LISTING SUBMITTED ELECTRONICALLY

The official copy of the sequence listing is submitted electronically via EFS-Web as an ASCII formatted sequence listing with the file "WO2014072233_Seq_Id" created on 5 May 2015 and having a size of 29 Kilobytes. The sequence listing contained in this ASCII formatted document forms part of the specification and is herein incorporated by reference in its entirety.

FIELD OF THE DISCLOSURE

The technology provided herein relates to novel immunoproteases suitable to induce apotosis in selected diseased target cells, comprising the serine protease granzyme M, and methods for using such cytolytic fusion proteins for the treatment of various diseases, in particular for the treatment of cancer.

BACKGROUND

In the treatment of tumors, autoimmune diseases, allergies and tissue rejection reactions, it is a disadvantage that the currently available medicaments, such as chemotherapeutic agents, corticosteroids and immunosuppressive agents, have a potential of side effects which is sometimes considerable, due to their relative non-specificity. It has been attempted to moderate this by various therapeutical concepts. Especially the use of immunotherapeutic agents is an approach, which resulted in an increase of the specificity of medicaments, especially in tumor treatment.

Immunotoxins are proteins used to treat e.g. cancer that are composed of an antibody or a fragment thereof linked to a toxin. The immunotoxin binds to a surface antigen on a cancer cell, enters the cell, and kills it. The most potent immunotoxins are made from bacterial and plant toxins. Refinements over many years have produced recombinant immunotoxins; these therapeutic proteins are made using protein engineering. Individual immunotoxins are designed to treat specific cancers. To date, most success has been achieved treating hematologic tumors. Obstacles to successful treatment of solid tumors include poor penetration into tumor masses and the immune response to the toxin component of the immunotoxin, which limits the number of doses that can be given. Strategies to overcome these limitations are being pursued.

The protein-based cell toxins which have been mostly used to date and are thus best characterized, are the bacterial toxins diphtheria toxin (DT) (Beaumelle, B. et al. 1992; Chaudhary, V. et al. 1990; Kuzel, T. M. et al. 1993; LeMaistre, C. et al. 1998), *Pseudomonas* exotoxin A (PE) (Fitz Gerald, D. J. et al. 1988; Pai, L. H. and Pastan, I. 1998), and the plant-derived ricin-A (Engert, A. et al. 1997; Matthey, B. et al. 2000; O'Hare, M. et al. 1990; Schnell, R. et al. 2000; Thorpe, P. E. et al. 1988; Youle, R. J. and Neville, D. M. J. 1980). The mechanism of cytotoxic activity is the same in all of these toxins despite of their different evolutionary backgrounds. The catalytic domain inhibits protein biosynthesis by a modification of the elongation factor EF-2, which is important to translation, or of the ribosomes directly, so that EF-2 can no longer bind (Endo, Y. et al. 1987; Iglewski, B. H. and Kabat, D. 1975).

In most of the constructs employed to date, the systemic application of immunotoxins results in more or less strong side effects. In addition to the "vascular leak" syndrome (Baluna, R. and Vitetta, E. S. 1997; Schnell, R. et al. 1998; Vitetta, E. S. 2000), thrombocytopenia, hemolysis, renal insufficiency and sickness occur, depending on the construct employed and the applied dosage. Dose-dependent and reversible liver damage could also be observed (Battelli, M. G. et al. 1996; Grossbard, M. L. et al. 1993; Harkonen, S. et al. 1987). In addition to the documented side effects, the immunogenicity of the constructs employed to be observed in the use of the immunoconjugates or immunotoxins is the key problem of immunotherapy (Khazaeli, M. B. et al. 1994). This applies, in particular, to the humoral defense against the catalytic domains employed, such as ricin (HARA) (Grossbard, M. L. et al. 1998), PE (Kreitman, R. J. et al. 2000), or DT (LeMaistre, E. F. et al. 1992). Theoretically, all non-human structures can provoke an immune response. Thus, the repeated administration of immunotoxins and immunoconjugates is subject to limitations. A logical consequence of these problems is the development of human immunotoxins, now named human cytolytic fusion proteins (Rybak, S. et al. 1992).

For example, cytotoxic lymphocyte granules contain perforin, a pore-forming protein, and a family of serine proteases, termed granzymes. Granzymes are serine proteases that are mainly expressed in cytotoxic T lymphocytes and natural killer cells.

Granzymes are involved in cell death by apoptosis (Coughlin et al, 2000) but also have other functions, including the regulation of B-cell proliferation, cleavage of extracellular matrix proteins, induction of cytokine secretion, activation of cytokines, control of viral infections (Trapani, 2001). For example, the serine protease granzyme B (GrB) (Lobe et al., 1986; Schmid and Weissman, 1987; Trapani et al., 1988) is integrally involved in apoptotic cell death induced in target cells upon their exposure to the contents of lysosome-like cytoplasmic granules (or cytolytic granules) found in cytotoxic T-lymphocytes (CTL) and natural killer (NK) cells (Henkart, 1985; Young and Cohn, 1986; Smyth and Trapani, 1995).

WO 01/80880 A1 discloses the use of the serine protease granzyme B in a cytolytic fusion protein (immunoprotease). The cytotoxic lymphocyte serine proteinase granzyme B induces apoptosis of abnormal cells by cleaving intracellular proteins at sites similar to those cleaved by caspases. However, granzyme B has a number of efficient natural inhibitors like Serpin B9 that prevent granzyme B-mediated apoptosis in certain cell types.

Thus, the technical problem underlying the present invention was to provide novel and improved cytolytic fusion proteins for the treatment of a disease.

SUMMARY OF THE DISCLOSURE

In a first aspect, embodiments of the disclosure provide cytolytic fusion proteins suitable to induce apotosis in a target cell comprising at least a first polypeptide comprising a binding structure to allow binding of the fusion protein to a specific target structure on the surface of a diseased cell, and at least a second polypeptide comprising a cytolytic serine protease, wherein the serine protease is granzyme M, modified forms, variants, functional fragments or mutants thereof.

In another aspect, the present disclosure pertains to pharmaceutical compositions comprising a cytolytic fusion protein according to the disclosure, also in combination with a second cytolytic fusion protein, also suitable to induce apotosis in a target cell comprising at least a first polypeptide comprising a binding structure to allow binding of the fusion protein to a specific target structure on the surface of a diseased cell, and at least a second polypeptide comprising a cytolytic serine protease, wherein the serine protease is granzyme B, modified forms, variants, functional fragments or mutants thereof.

Furthermore, the disclosure relates to medicaments comprising a cytolytic fusion protein or a composition of the present disclosure in combination with a pharmacologically acceptable carrier or diluent and their use in treating a malignant disease, an allergy, autoimmune reaction, tissue rejection reaction, or chronic inflammation reaction, in particular cancer.

In another aspect, the present disclosure relates to methods for preparing the cytolytic fusion protein comprising culturing host cells and isolating the cytolytic fusion protein from the culture.

Further, embodiments of this disclosure relate generally to the use of the cytolytic fusion protein and compositions according to the present disclosure for the induction of cell death, in particular induction of cell death by apoptosis. Advantageously, cytolytic fusion protein and of this disclosure are used for treating cancer.

Before the disclosure is described in detail, it is to be understood that this disclosure is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. It is moreover to be understood that, in case parameter ranges are given which are delimited by numeric values, the ranges are deemed to include these limitation values.

BRIEF DESCRIPTION OF THE DRAWINGS

FIG. 18 shows in A) the nucleic acid sequence of wild type human granzyme M (SEQ ID NO.1) and in B) the amino acid sequence of wild type human granzyme M (SEQ ID NO.2).

FIG. 19 shows in A) the nucleic acid sequence of the cytolytic fusion protein variant Gm-H22(scFv) (SEQ ID NO.3) and in B) the respective amino acid sequence (SEQ ID NO.4).

FIG. 20 shows in A) the nucleic acid sequence of the cytolytic fusion protein variant Gm-Ki4(scFv) (SEQ ID NO.5) and in B) the respective amino acid sequence (SEQ ID NO.6).

FIG. 21 shows in A) the nucleic acid sequence of the cytolytic fusion protein variant Gm-425(scFv) (SEQ ID NO.7) and in B) the respective amino acid sequence (SEQ ID NO.8).

FIG. 22 shows in A) the nucleic acid sequence of the cytolytic fusion protein variant Gm-RFT5(scFv) (SEQ ID NO.9) and in B) the respective amino acid sequence (SEQ ID NO.10).

DETAILED DESCRIPTION OF THIS DISCLOSURE

Disclosed herein are cytolytic fusion proteins and compositions useful for the treatment of malignant diseases, allergies, autoimmune reactions, tissue rejection reactions, and/or chronic inflammation reactions by inducing apotosis in a specific diseased target cell.

The present disclosure pertains to the use of a novel immunoprotease with a cytotoxic/cytolytic moiety called granzyme M for inducing apoptosis in targeted diseased cells. The inventors found that in addition to the known potential of granzyme B based immunoproteases, also granzyme M fused to different specific binders is a potent anti-tumoral cytotoxic agent.

According to the present disclosure, in some advantageous embodiments the inventors cloned isolated granzyme M to single chain fragments specific for binding to tumor markers including anti-CD64, anti-CD30, anti-EGFR and anti-CD25 and expressed these immunotherapeutic agents in HEK293T cells. After affinity purification, the identity and purity of the obtained proteins were confirmed by SDS-PAGE followed by Coomassie staining and Western Blotting. Specific binding was verified by flow cytometry and the specific anti-tumoral cytotoxicity was finally demonstrated in apoptosis and viability assays in vitro.

Figure 16:
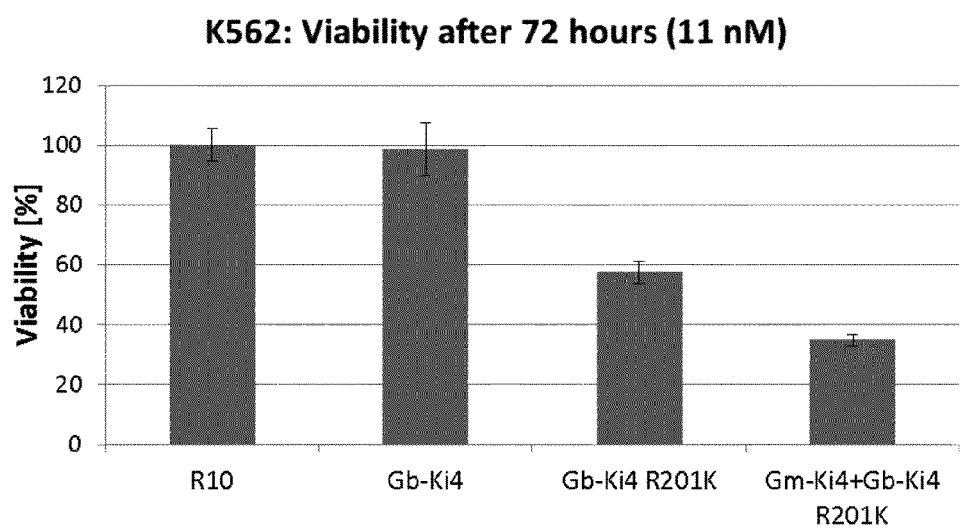
FIG. 16 shows the results of viability assays on PI9$^+$ K562 cells.

Surprisingly, the inventors could demonstrate that granzyme M is a new promising human pro-apoptotic enzyme suitable for cancer therapy. Furthermore, the inventors found that the novel immunoproteases can be used as well in context of other diseases, such as inflammation. In particular, the combination of granzyme B and granzyme M based cytolytic fusion proteins leads to an improved therapeutic approach. As shown in FIG. 16, the co-incubation of a cytolytic fusion protein based on a granzyme B variant (Gb-Ki4 R201K) and a cytolytic fusion protein based on w/t granzyme M (Gm-Ki4) has an improved effect on induced cell death. In one aspect, the inventors used the human protein Granzyme M for targeting cancer cells including primary leukemic cells, to avoid the immunogenicity associated with bacterial or plant toxins in human.

As mentioned above, the cytotoxic/cytolytic component used in the cytolytic fusion proteins according to the present disclosure is granzyme M. Granzyme M (Gm) is a neutral serine protease, also known as Met-ase, Lymphocyte Met-ase 1, Natural killer cell Met-ase.

Granzyme M cleaves specifically after leucine at P1 position[5] and is mainly expressed within NK cells, NKT cells, γd-T cells and CD8+ effector T cells[6,7]. It has been found that prominent substrates of granzyme M present within tumor cells include ICAD, PARP, HSP75, ezrin, survivin, α-tubulin[8-11].

Surprisingly, as shown in the results of the present disclosure granzyme M fused to different specific structures works as a highly potent cytotoxic agent, in particular as an anti-tumoral cytotoxic agent.

Some advantageous embodiments pertains to isolated cytolytic fusion proteins suitable to induce apotosis in a target cell comprising at least a first isolated polypeptide comprising a binding structure to allow binding of the fusion protein to a specific target structure on the surface of a diseased cell, and at least a second isolated polypeptide comprising a cytolytic serine protease, wherein the serine protease is granzyme M, modified forms, variants, functional fragments or mutants thereof.

The term "modified form" or "variant" means that the enzyme has been modified from its original form (parent/wildtype, wt) but retains the same enzymatic functional characteristics as that of human wildtype granzyme M.

The term "fusion proteins" comprises all proteins derived from the human wildtype granzyme M or any variant thereof by covalently fusing additional amino-acid sequences at the C- and/or N-terminus. The source and composition of the additional amino-acid sequence is either natural from any living organisms or virus or unnatural. In particular, the fusion protein may be a "recombinant" polypeptide, which is defined either by its method of production or its structure. In reference to its method of production, e.g., a product made by a process, the process involved uses recombinant nucleic acid techniques. In reference to structure, recombinant polynucleotides or polypeptides contain sequences from different sources. In particular, it encompasses polypeptides made by generating a sequence comprising two or more fragments, which are not naturally contiguous or operably linked to each other. Thus, for example, products made by transforming cells with any unnaturally occurring vector are encompassed. The term may also be construed to mean fusion protein which has been generated by the synthesis of a DNA molecule encoding the fusion protein and which DNA molecule expresses a fusion protein, or an amino acid sequence specifying the fusion protein, wherein the DNA or amino acid sequence has been obtained using synthetic DNA or amino acid sequence technology which is available and well known in the art. In an embodiment, cytolytic fusion protein according to the present disclosure is a recombinant and/or synthetic fusion protein.

The term "functional fragment" or "effective fragment" means a fragment or portion of the human wildtype granzyme M or variants thereof that retains the same enzymatic function or effect.

The term "polynucleotide" corresponds to any genetic material of any length and any sequence, comprising single-stranded and double-stranded DNA and RNA molecules, including regulatory elements, structural genes, groups of genes, plasmids, whole genomes and fragments thereof.

The term "granzyme M variant" means any granzyme M molecule obtained by site-directed or random mutagenesis, insertion, deletion, recombination and/or any other protein engineering method, which leads to granzyme M that differ in their amino acid sequence from the human wildtype granzyme M. The terms "wildtype granzyme M", "wildtype enzyme", or "wildtype" in accordance with the disclosure describe a serine protease enzyme with an amino acid sequence found in nature or a fragment thereof.

The term "granzyme B variant" means any granzyme B molecule obtained by site-directed or random mutagenesis, insertion, deletion, recombination and/or any other protein engineering method, which leads to granzyme M that differ in their amino acid sequence from the human wildtype granzyme B. The terms "wildtype granzyme B", "wildtype enzyme", or "wildtype" in accordance with the disclosure describe a serine protease enzyme with an amino acid sequence found in nature or a fragment thereof.

The term "isolated" describes any molecule separated from its natural source.

The term "mutation" refers to the substitution or replacement of single or multiple nucleotide triplets, insertions or deletions of one or more codons, homologous or heterologous recombination between different genes, fusion of additional coding sequences at either end of the encoding sequence, or insertion of additional encoding sequences or any combination of these methods, which result in a polynucleic acid sequence encoding the desired protein. Thus, the term "mutations" also refers to all of the changes in the polypeptide sequence encoded by the polynucleic acid sequence modified by one or more of the above-described changes.

The term "nucleic acid molecule" or "nucleic acid" is intended to indicate any single- or double stranded nucleic acid molecule of cDNA, genomic DNA, synthetic DNA or RNA, Peptide nucleic acid (PNA) or LNA origin.

The term "stringent conditions" relates to conditions under which a probe will hybridize to its target sub-sequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion (or other salts) at pH 7.0 to 8.3 and the temperature is at least about 30° C. for short probes (e.g. 10 to 50 nucleotides) and at least about 60° C. for longer probes. Stringent conditions may also be achieved with the addition of destabilizing agents, such as formamide and the like.

The term "variant of the nucleic acid molecule" refers herein to a nucleic acid molecule that is substantially similar in structure and biological activity to a nucleic acid molecule according to one of the claimed sequences.

The term "homologue of the nucleic acid molecule" refers to a nucleic acid molecule the sequence of which has one or more nucleotides added, deleted, substituted or otherwise chemically modified in comparison to a nucleic acid molecule according to one of the claimed sequences, provided always that the homologue retains substantially the same binding properties as the latter.

The term "derivative" as used herein, refers to a nucleic acid molecule that has similar binding characteristics to a target nucleic acid sequence as a nucleic acid molecule according to one of the claimed sequences.

A "target cell" as used in the present disclosure may be any cell that has a specific receptor for an antigen or antibody or hormone or drug, or is the focus of contact by a virus or phagocyte or nerve fiber etc. In particular, a "target cell" according to the present disclosure is a diseased cell in mammalian, in particular a human diseased cell.

As used herein the term "diseased cell" refers to any cell that fails to operate in its naturally occurring condition or normal biochemical fashion. These cells should be capable of causing disease. For instance, the word shall include cells that are subject to uncontrolled growth, cellular mutation, metastasis or infection. The term shall also include cells that have been infected by a foreign virus or viral particle, bacteria, bacterial exotoxins or endotoxins, prions, or other similar type living or non-living materials. The term may in particularly refer to cancer cells or cells infected by the poliovirus, rhinovirus, piconavirus, influenza virus, or a retrovirus such as the human immunodeficiency virus (HIV).

The term "tumor-associated antigen" includes antigens that are highly correlated with certain tumor cells. They are not usually found, or are found to a lesser extent, on normal cells.

The term "immunotoxin" refers to a complex comprising a targeting portion linked to a bacterial/plant toxin.

The term "cytolytic fusion protein" or "human cytolytic fusion protein" refers to a fusion protein comprising a human enzyme suitable for the dissolution or destruction of a target cell.

The term "immunoprotease" refers to a cytolytic fusion protein comprising a protease with a human origin.

The term "plasmid", "vector system" or "expression vector" means a construct capable of in vivo or in vitro expression. In the context of the present disclosure, these constructs may be used to introduce genes encoding enzymes into host cells.

The term "host cell" in relation to the present disclosure includes any cell that comprises either the nucleic acid molecule or an expression vector as described above and which is used in the recombinant production of an enzyme having the specific properties as defined herein or in the methods of the present disclosure.

It is also understood that the present disclosure comprises all molecules that are derived from the polynucleotides of the disclosure and all variants thereof described in this application, by posttranslational processing compared to the genetically encoded amino acid sequence. These posttranslational modifications comprise, but are not limited to, proteolytic cleavage of N-terminal sequences such as leader and/or pro-sequences, proteolytic removal of C-terminal extensions, N- and/or O-glycosylation, lipidation, acylation, deamidation, pyroglutamate formation, phosphorylation and/or others, or any combination thereof, as they occur during production/expression by the native host or any suitable expression host. These post-translational modifications may or may not have an influence on the physical or enzymatic properties of the enzymes as explored herein.

The nucleic acid molecules of the present disclosure may comprise a nucleotide sequence that encodes for SEQ ID NO:1 a variant, modified form, homologue or derivative thereof. In some advantageous embodiments, the nucleic acid molecules of the present disclosure may comprise a nucleotide sequence that encodes for SEQ ID NO:3, SEQ ID NO:5, SEQ ID NO:7 and/or SEQ ID NO:9.

In particular, the disclosure provides a plasmid or vector system comprising a nucleic acid sequence encoding a cytolytic fusion protein as described herein or a homologue or derivative thereof.

Embodiments of the present disclosure pertains to cytolytic fusion proteins comprising a serine protease having at least 90 percent identity to SEQ ID NO: 2. In some advantageous embodiments, the cytolytic fusion protein comprises an amino acid sequence selected from the group of SEQ ID NO. 4, SEQ ID NO. 6, SEQ ID NO. 8 and SEQ ID NO. 10.

Further embodiments of the present disclosure pertain to cytolytic fusion proteins comprising a serine protease having at least 85%, at least 90%, at least 95%, at least 99 percent identity to SEQ ID NO: 2. In some advantageous embodiments, the cytolytic fusion protein comprises an amino acid sequence having at least 85%, at least 90%, at least 95%, at least 99 percent identity to SEQ ID NO. 4, SEQ ID NO. 6, SEQ ID NO. 8 and SEQ ID NO. 10.

There is no requirement that the cytolytic fusion proteins of the present disclosure comprise a full-length native polypeptide sequence of the serine protease granzyme M. Rather, the polypeptide can also have a sequence that is modified from a native polypeptide sequence using the techniques known to those of skill in the art and/or taught in this specification. In some particular embodiments, the polypeptide is an enzyme variant that comprises a sequence that has serine protease function. Those of ordinary skill in the art will understand that it is possible to reduce, increase or decrease the number of amino acids in polypeptide variants according to the present disclosure, as long as the active site and activity of the polypeptide having serine protease activity are maintained. For example, there are a wide variety of variants that can be prepared to meet the needs according to the present disclosure and the teachings of this paragraph and the remainder of the specification can be used to prepare variants based on a large number of polypeptides that have granzyme M activity.

Therefore, the disclosure pertains to modified form of the polypeptide comprising granzyme M which has at least a minimum percentage sequence identity and/or percent homology to the serine proteases of SEQ ID NO. 2, wherein the minimum percent identity and/or homology is at least 75%, at least 80%, at least 85%, at least 90%, at least 93%, at least 96%, at least 97%, at least 98% or at least 99%.

The polypeptides having serine protease activity according to the present disclosure may, in addition to the serine protease active center, comprise a leader segment. Typically, these leader segments will be positively charged amino acid segments that facilitate protein translocation into the cytosol of the cell. Examples of such sequences include, but are not limited to, an IG-kappa leader sequence. Of course, it is possible for one of ordinary skill to design and test an almost unlimited number of leader sequences that can be used in the invention. In most cases, these sequences simply require a relatively short segment of primarily positively charged amino acids. For a general review of such leader sequences, one can review Ford et al. 2001.

As mentioned above, the cytolytic fusion proteins comprise at least a first polypeptide with a binding structure for binding the fusion protein to a specific target structure on the surface of the target cell.

The specific target structure may be cancer cell specific structure or a disease specific structure of pathogenic substances or pathogenic matter.

In some embodiments, the binding structure comprises moieties which are affinity moieties from affinity substances or affinity substances in their entirety selected from the group consisting of antibodies, antibody fragments, receptor ligands, enzyme substrates, lectins, cytokines, lymphokines, interleukins, angiogenic or virulence factors, allergens, peptidic allergens, recombinant allergens, allergen-idiotypical antibodies, autoimmune-provoking structures, tissue-rejection-inducing structures, immunoglobulin constant regions and their derivatives, mutants or combinations thereof.

For example, in certain embodiments, the binding structures as cell targeting moieties for use in the current disclosure are antibodies. In general the term antibody includes, but is not limited to, polyclonal antibodies, monoclonal antibodies, single chain antibodies, humanized antibodies, minibodies, dibodies, tribodies as well as antibody fragments, such as Fab', Fab, F(ab')2, single domain antibodies and any mixture thereof, in some cases it is preferred that the cell targeting moiety is a single chain antibody (scFv). In a related embodiment, the cell-targeting domain may be an avimer polypeptide. Therefore, in certain cases the cell targeting constructs of the invention are fusion proteins comprising a polypeptide according to the present disclosure and a scFv or an avimer. In some very specific embodiments the cell-targeting construct is a fusion protein comprising granzyme M fused to a single chain antibody.

In certain other embodiments, the binding structure may be a growth factor. For example, transforming growth factor, epidermal growth factor, insulin-like growth factor, fibroblast growth factor, B lymphocyte stimulator (BLyS), heregulin, platelet-derived growth factor, vascular endothelial growth factor (VEGF), or hypoxia inducible factor may be used as a cell-targeting moiety according to the disclosure. These growth factors enable the targeting of constructs to cells that express the cognate growth factor receptors.

In further aspects of the invention, the binding structure may be a hormone. Some examples of hormones for use in the disclosure include, but are not limited to, human chorionic gonadotropin, gonadotropin releasing hormone, an androgen, an estrogen, thyroid-stimulating hormone, follicle-stimulating hormone, luteinizing hormone, prolactin, growth hormone, adrenocorticotropic hormone, antidiuretic hormone, oxytocin, thyrotropin-releasing hormone, growth hormone releasing hormone, corticotropin-releasing hormone, somatostatin, dopamine, melatonin, thyroxine, calcitonin, parathyroid hormone, glucocorticoids, mineralocorticoids, adrenaline, noradrenaline, progesterone, insulin, glucagon, amylin, erythropoitin, calcitriol, calciferol, atrial-natriuretic peptide, gastrin, secretin, cholecystokinin, neuropeptide Y, ghrelin, PYY3-36, insulin-like growth factor-1, leptin, thrombopoietin and angiotensinogen.

In further embodiments of the present disclosure, binding structures may also be cytokines. For example IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, or IL-36, granulocyte-colony stimulating factor, macrophage-colony stimulating factor, granulocyte-macrophage colony stimulating factor, leukemia inhibitory factor, erythropoietin, granulocyte macrophage colony stimulating factor, oncostatin M, leukemia inhibitory factor, IFN-GAMMA, IFN-ALPHA, IFN-BETA, LT-BETA, CD40 ligand, Fas ligand, CD27 ligand, CD30 ligand, 4-1BBL, TGF-BETA, IL Ialpha, IL-I BETA, IL-1RA (Interleukin 1 receptor antagonist), MIF and IGIF (IFN-gamma inducing factor) may all be used as targeting moieties according to the disclosure.

As mentioned above, in certain aspects of the disclosure the binding structure may be a cell-targeting moiety, in particular a cancer cell-targeting moiety. It is well known that certain types of cancer cells aberrantly express surface molecules that are unique as compared to surrounding tissue. Thus, cell-targeting moieties that bind to these surface molecules enable the targeted delivery of the polypeptides of the present disclosure specifically to the cancers cells. For example, a cell targeting moiety may bind to and be internalized by a lung, breast, brain, prostate, spleen, pancreatic, cervical, ovarian, head and neck, esophageal, liver, skin, kidney, leukemia, bone, testicular, colon or bladder cancer cell. The skilled artisan will understand that the effectiveness of cancer cell targeted polypeptides of the present disclosure may, in some cases, be contingent upon the expression or expression level of a particular cancer marker on the cancer cell. Thus, in certain aspects there is provided a method for treating a cancer with targeted polypeptides of the present disclosure comprising determining whether (or to what extent) the cancer cell expresses a particular cell surface marker and administering polypeptide targeted therapy (or another anticancer therapy) to the cancer cells depending on the expression level of a marker gene or polypeptide.

In advantageous embodiments, the binding structure belongs to the group of antigen binding polypeptides/proteins targeting cell type specific markers/structures, in particular the binding structure is directed against cancer cell specific structures, disease specific structures of pathogenic substances or pathogenic matter or the binding structure is binding to soluble markers of disease/environment/food and feed safety or biodefense.

In particular, in advantageous embodiments the binding structure comprises moieties which are affinity moieties from affinity substances or affinity substances in their entirety selected from the group consisting of antibodies, antibody fragments, receptor ligands, enzyme substrates, lectins, cytokines, lymphokines, interleukins, angiogenic or virulence factors, allergens, peptidic allergens, recombinant allergens, allergen-idiotypical antibodies, autoimmune-provoking structures, tissue-rejection-inducing structures, immunoglobulin constant regions and their derivatives, mutants or combinations thereof. In further advantageous embodiments, the antibody fragment is a Fab, an scFv; a single domain, or a fragment thereof, a bis scFv, $Fab_2$, $Fab_3$, minibody, maxibody, diabody, triabody, tetrabody or tandab, in particular a single-chain variable fragment (scFv).

In advantageous embodiments of the present disclosure, the scFv is specific for the CD64, CD25, CD30 and/or EGF-receptor.

CD64 (Cluster of Differentiation 64) is a type of integral membrane glycoprotein known as a Fc receptor that binds monomeric IgG-type antibodies with high affinity (Hulett M et al., 1998, Mol Immunol 35). It is also known as Fc-gamma receptor 1 (FcγRI). After binding IgG, CD64 interacts with an accessory chain known as the common γ chain (γ chain), which possesses an ITAM motif that is necessary for triggering cellular activation. Structurally CD64 is composed of a signal peptide that allows its transport to the surface of a cell, three extracellular immunoglobulin domains of the C2-type that it uses to bind antibody, a hydrophobic transmembrane domain, and a short cytoplasmic tail. There are three distinct (but highly similar) genes in humans for CD64 called FcγRIA (CD64A), FcγRIB (CD64B), and FcγRIC (CD64C) that are located on chromosome 1. These three genes produce six different mRNA transcripts; two from CD64A, three from CD64B, and one from CD64C; by alternate splicing of the genes. The 72 kDa glycoprotein CD64 (FcγRI) is the mediator of endocytosis and phagocytosis, antibody-dependent cellular cytotoxicity and production of cytokines and superoxide. It is involved in inflammatory diseases and also over-expressed on the surface of leukemic cells.

CD30, also known as TNFRSF8, is a cell membrane protein of the tumor necrosis factor receptor family and tumor marker. This receptor is expressed by activated, but not by resting, T and B cells. TRAF2 and TRAF5 can interact with this receptor, and mediate the signal transduction that leads to the activation of NF-kappaB. It is a positive regulator of apoptosis, and also has been shown to limit the proliferative potential of autoreactive CD8+ effector T cells and protect the body against autoimmunity. Two alternatively spliced transcript variants of this gene encoding distinct isoforms have been reported. CD30 is associated with anaplastic large cell lymphoma. It turned out to be a promising target for the treatment of Hodgkin lymphoma in previous studies (Schwab, Stein et al. 1982; Gruss, Pinto et al. 1996).

CD25 is the alpha chain of the IL-2 receptor. It is a type I transmembrane protein present on activated T cells, activated B cells, some thymocytes, myeloid precursors, and oligodendrocytes that associates with CD122 to form a heterodimer that can act as a high-affinity receptor for IL-2. CD25 is expressed in most B-cell neoplasms, some acute nonlymphocytic leukemias, neuroblastomas, and tumor infiltrating lymphocytes. Its soluble form, called sIL-2R may be elevated in these diseases and is occasionally used to track disease progression. CD25 is efficiently induced upon T cell activation, not detectable on resting T cells, B cells or monocytes and is overexpressed on Hodgkin and Reed-Sternberg cells. It is also present in adult T cell leukemia, peripheral T cell leukemia/lymphomas, cutaneous T cell lymphoma, B cell non-Hodgkin's lymphomas, hairy cell leukemia, chronic lymphocytic leukemia, and acute myeloblastic leukemia[18].

Epidermal Growth Factor Receptor (EGF Receptor, or EGFR) is a cell-surface glycoprotein composed of a single polypeptide chain that binds the peptide Epidermal Growth Factor (EGF). The EGF Receptor consists of an extracellular ligand binding domain, a single transmembrane region and a cytoplasmic intrinsic tyrosine kinase domain. Upon ligand binding, the EGF Receptor autophosphorylates, activating the tyrosine kinase domain of the EGF Receptor. The EGFR and EGF-like peptides are often over-expressed in human carcinomas. For example, A431 cells are a model cell line (epidermoid carcinoma) used in biomedical research. More specifically, they are used in studies of the cell cycle and cancer-associated cell signaling pathways since they express abnormally high levels of the EGFR.

In some embodiments, the cytolytic fusion proteins of the present disclosure comprise one or more supplementary components in addition to the binding structure and the serine protease. From his former experience, the skilled person knows that additional features and properties can have a critical importance to the efficient preparation and/or effectiveness of the cytolytic fusion proteins of the present disclosure. Due to the distinctness of the diseases to be treated with the cytolytic fusion according to the disclosure, an adaptation of the cytolytic fusion proteins to the respective particular circumstances may be necessary.

As supplementary component the cytolytic fusion proteins may comprise one or more further polypeptide(s) selected from the group consisting of a leader sequence capable of controlling protein biosynthesis, a protein tag, a translocation domain amphiphatic sequence capable of translocating the fusion protein into the target cell and a synthetic pro-serine protease amphiphatic sequence capable of intracellular activation of the serine protease.

In advantageous embodiments, the additional polypeptide is a leader sequence for secretory expression and/or the component polypeptide is a enterokinase cleavage site enabling activation of the granzyme M protease and/or the polypeptide is a HIS tag or affinity tag, enabling purification of the cytolytic fusion proteins.

As used herein, "protein tags" are peptide sequences genetically grafted onto a recombinant protein. In general these tags are removable by chemical agents or by enzymatic means, such as proteolysis or splicing.

Affinity tags are appended to proteins so that they can be purified from their crude biological source using an affinity technique. These include chitin binding protein (CBP), maltose binding protein (MBP), and glutathione-S-transferase (GST). In an advantageous embodiment, a poly(His) tag is used in the recombinant fusion proteins according to the present disclosure.

Solubilization tags may also be used, especially if the recombinant fusion proteins are expressed in chaperone-deficient species such as E. coli, to assist in the proper folding in proteins and keep them from precipitating. These include thioredoxin (TRX) and poly(NANP). Some affinity tags have a dual role as a solubilization agent, such as MBP, and GST.

Chromatography tags may be used to alter chromatographic properties of the fusion proteins to afford different resolution across a particular separation technique. Often, these consist of polyanionic amino acids, such as FLAG-tag.

Epitope tags are short peptide sequences which may be chosen because high-affinity antibodies can be reliably produced in many different species. These are usually derived from viral genes, which explain their high immunoreactivity. Epitope tags include V5-tag, c-myc-tag, and HA-tag. These tags are particularly useful for western blotting, immunofluorescence and immunoprecipitation experiments, although they also find use in antibody purification.

Fluorescence tags may be used to give visual readout on a protein. GFP and its variants are the most commonly used fluorescence tags. More advanced applications of GFP include their usage as a folding reporter (fluorescent if folded, colorless if not).

In some embodiments, the cytolytic fusion protein according to the present disclosure comprises a further cytolytic serine protease, wherein the serine protease is preferably granzyme B, a mutant or a homologue thereof.

In a further embodiment of the disclosure there is provided an isolated nucleic acid sequence comprising sequence encoding a polypeptide as described supra. Thus, a nucleic acid sequence encoding any of the polypeptides or polypeptide fusion proteins described herein are also included as part of the instant invention. The skilled artisan will understand that a variety of nucleic acid sequence may be used to encode identical polypeptides in view of the degeneracy of genetic code. In certain cases for example the codon encoding any particular amino acid may be altered to improve cellular expression.

The nucleic acid molecules according to the present disclosure are selected from the group consisting of
- a) a nucleic acid molecule encoding the cytolytic fusion protein according to the present disclosure;
- b) a nucleic acid molecule encoding for a modified form of cytolytic fusion protein according to the present disclosure, preferably in which one or more amino acid residues are conservatively substituted;
- c) a nucleic acid molecule that is a fraction, variant, homologue, derivative, or fragment of the nucleic acid molecule presented as SEQ ID NO:3, SEQ ID NO:5, SEQ ID NO:7 or SEQ ID NO:9;
- d) a nucleic acid molecule that is capable of hybridizing to any of the nucleic acid molecules of a)-c) under stringent conditions;
- e) a nucleic acid molecule that is capable of hybridizing to the complement of any of the nucleic acid molecules of a)-d) under stringent conditions;
- f) a nucleic acid molecule having a sequence identity of at least 95% with any of the nucleic acid molecules of a)-e) and encoding for a cytolytic fusion protein;
- g) a nucleic acid molecule having a sequence identity of at least 70% with any of the nucleic acid molecules of a)-f) and encoding for a cytolytic fusion protein;
- h) or a complement of any of the nucleic acid molecules of a)-g).

In preferred aspects, a nucleic acid sequence encoding a cytolytic fusion protein of this disclosure is comprised in an expression cassette. As used herein the term "expression cassette" means that additional nucleic acids sequences are included that enable expression of the polypeptides in a cell, or more particularly in a eukaryotic cell. Such additional sequences may, for example, comprise a promoter, an enhancer, intron sequences or a polyadenylation signal sequence.

Figure 1:
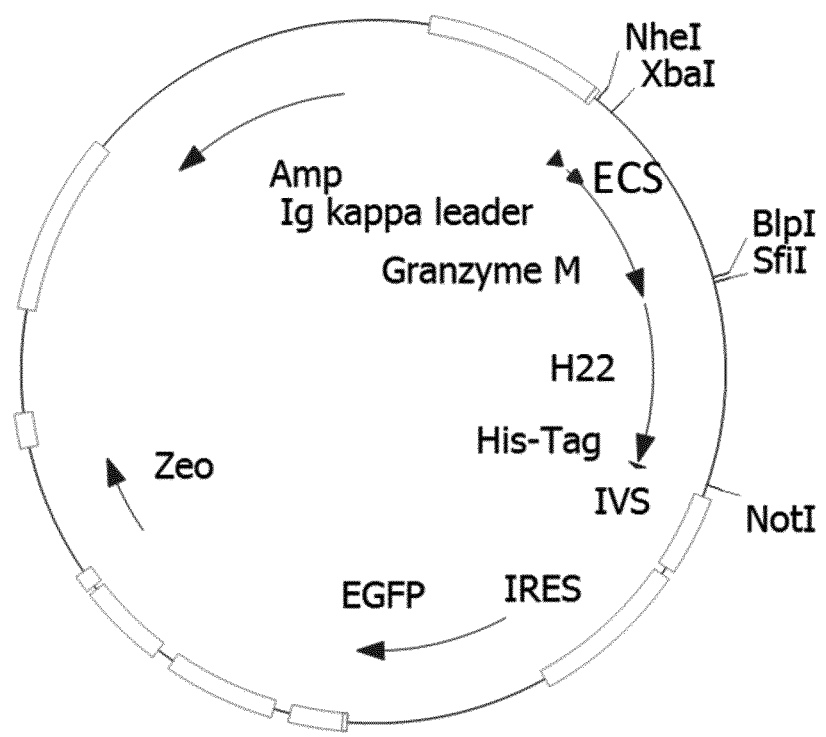
FIG. 1 shows the schematic structure of the pMS plasmid containing the sequence for embodiments of the cytolytic fusion proteins according to the present disclosure.

In still further aspects of the disclosure a coding sequence for the polypeptides may be comprised in an expression vector such as a viral expression vector (see FIG. 1). Viral expression vectors for use according to the invention include but are not limited to adenovirus, adeno-associated virus, herpes virus, SV-40, retrovirus and vaccinia virus vector systems.

Embodiments pertain also to compositions comprising a cytolytic fusion protein of the present disclosure, in particular to pharmaceutical, diagnostic or cosmetic compositions.

In further embodiments, the compositions comprise a second cytolytic fusion protein, also suitable to induce apotosis in a target cell comprising at least a first polypeptide comprising a binding structure to allow binding of the fusion protein to a specific target structure on the surface of a diseased cell, and at least a second polypeptide comprising a cytolytic serine protease, wherein the serine protease is granzyme B, a mutant or a homologue thereof.

In some embodiments, the binding structure comprised in the first polypeptide of the first cytolytic fusion protein comprising granzyme M is different to the first polypeptide of the second cytolytic fusion protein comprising granzyme B. In advantageous embodiments, the first and the second cytolytic fusion protein binds to different specific target structures on the surface of the same target cell.

As shown in FIG. 16, the co-incubation of a cytolytic fusion protein based on a granzyme B variant (Gb-Ki4 R201K) and a cytolytic fusion protein based on w/t granzyme M (Gm-Ki4) has an improved effect on induced cell death. In further advantageous embodiments, the combination of Gm-RFT5(scFv) and Gb-Ki4(scFv), or Gb-RFT5 (scFv) and Gm-Ki4(scFv), or Gb-RFT5(scFv) and Gm-RFT5(scFv) on L540 cells which are both CD30 and CD25 positive shows an additive effect an improved effect on induced cell death. Therefore, compositions comprising these combinations of cytolytic fusion proteins are useful for inducing apoptosis in diseased target cells, in particular for the treatment of cancer.

The composition according to the present disclosure may be a pharmaceutical, diagnostic or cosmetic composition and can be used with a "pharmaceutically acceptable carrier" which includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art. A pharmaceutically acceptable carrier is preferably formulated for administration to a human, although in certain embodiments it may be desirable to use a pharmaceutically acceptable carrier that is formulated for administration to a non-human animal, such as a canine, but which would not be acceptable (e.g., due to governmental regulations) for administration to a human. Except insofar as any conventional carrier is incompatible with the active ingredient, its use in the therapeutic or pharmaceutical compositions is contemplated.

The actual dosage amount of a composition of the present invention administered to a subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

By "pharmaceutically effective" is meant the ability to cure, reduce or prevent one or more clinical symptoms caused by or associated with the diseased cells in the patient mammal, including, but not limited to, uncontrolled cell proliferation, bacteria infection, and virus infection.

In advantageous embodiments, polypeptide according to the disclosure are used for preparing a medicament for preventing or treating a disease like allergy, autoimmune reaction, tissue rejection reaction, or chronic inflammation reaction, preferably cancer.

Thus, in a specific embodiment, there is provided a method for treating a patient with cancer comprising administering to the patient an effective amount of a therapeutic composition comprising a cytolytic fusion protein according to the present disclosure or a nucleic acid expression vector encoding a cytolytic fusion protein as described supra. In preferred aspects, methods described herein may be used to treat a human patient.

As described above, in certain aspects, the disclosure provides methods for treating cancer. Thus, in certain cases, described methods may be used to limit or reduce tumor cells by apoptosis thereby reducing tumor growth or metastasis. A variety of cancer types may be treated with methods of the present disclosure, for example a cancer for treatment may be a bladder, blood, bone, bone marrow, brain, breast, colon, esophagus, eye, gastrointestinal, gum, head, kidney, liver, lung, nasopharynx, neck, ovary, prostate, skin, stomach, testis, tongue, or uterus cancer. Furthermore additional anticancer therapies may be used in combination or in conjunction with methods of the invention. Such additional therapies may be administered before, after or concomitantly with methods of the disclosure. For example an additional anticancer therapy may be chemotherapy, surgical therapy, an immunotherapy or a radiation therapy.

It is contemplated that polypeptides, compositions and/or complexes of the disclosure may be administered to a patient locally or systemically. For example, methods of the invention may involve administering a composition topically, intravenously, intradermally, intraarterially, intraperitoneally, intralesionally, intracranially, intraarticularly, intraprostaticaly, intrapleurally, intratracheally, intraocularly, intranasally, intravitreally, intravaginally, intrarectally, intramuscularly, intraperitoneally, subcutaneously, subconjunctival, intravesicularlly, mucosally, intrapericardially, intraumbilically, intraocularally, orally, by inhalation, by injection, by infusion, by continuous infusion, by localized perfusion bathing target cells directly, via a catheter, or via a lavage.

Further, embodiments of this disclosure relate to the use of the cytolytic fusion proteins and compositions according to the present disclosure for the preparation of a pharmaceutical, diagnostic or cosmetic composition. In some embodiments, the disclosure pertains to medicaments comprising the cytolytic fusion protein or the composition of the disclosure in combination with a pharmacologically acceptable carrier or diluent as defined above.

In another aspect, the disclosure relates to methods of treating a malignant disease, an allergy, autoimmune reaction, tissue rejection reaction, or chronic inflammation reaction comprising administering an effective amount of a cytolytic fusion protein or a composition according to the present disclosure to a patient in need thereof.

Figure 2:
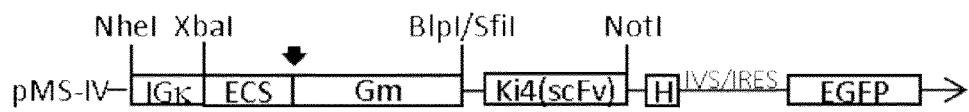
FIG. 2 shows a schematic structure of the DNA construct encoding for embodiments of cytolytic fusion proteins according to the present disclosure.
Figure 2:
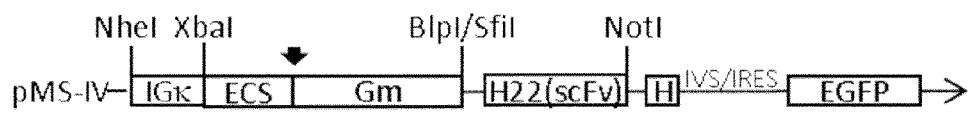
Figure 2:
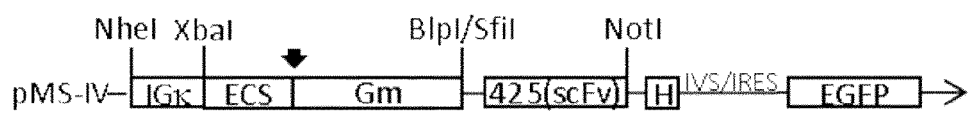
Figure 2:
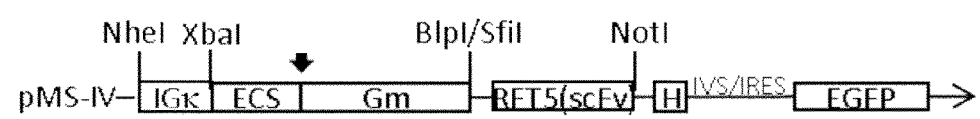

Advantageous examples for the cytolytic fusion proteins according to the present disclosure are shown in FIG. 2:

Anti-CD30 scFv "Ki-4" against Hodgkin lymphoma cell lines L540, L428, L1236 and CML cell line K562

Anti-CD64 scFv "H22" against AML cell lines HL60 and CD64$^+$ primary cells from CMML patients Anti-EGFR scFv "425" against human epidermoid carcinoma cell line A431

Anti-CD25 scFv "RFT5" against Hodgkin lymphoma cell line L540

Furthermore, cellular compartments or host cells which synthesize complete cytolytic fusion proteins according to the disclosure or individual components thereof after transformation or transfection with the nucleic acid molecules or vectors according to the disclosure are also claimed according to the invention.

The cellular compartments or host cells according to the disclosure are of either prokaryotic origin, especially from *E. coli, B. subtilis, S. carnosus, S. coelicolor, Marinococcus* sp., or eukaryotic origin, especially from *Saccharomyces* sp., *Aspergillus* sp., *Spodoptera* sp., *P. pastoris*, primary or cultivated mammal cells, eukaryotic cell lines (e.g., CHO, Cos or 293) or plant systems (e.g. *N. tabacum*). In an advantageous embodiment, the cytolytic fusion proteins are expressed in HEK293T cells.

The following methods and examples are offered for illustrative purposes only, and are not intended to limit the scope of the present disclosure in any way.

METHODS AND EXAMPLES

In the following examples, materials and methods of the present disclosure are provided including the determination of catalytic properties of the cytolytic fusion proteins according to the present disclosure. It should be understood that these examples are for illustrative purpose only and are not to be construed as limiting this disclosure in any manner. All publications, patents, and patent applications cited herein are hereby incorporated by reference in their entirety for all purposes.

Example 1

Recombinant Techniques for Generation of Granzyme M Based Immunotoxins

The coding sequence for granzyme M was amplified from human blood-derived RNA. The construction of the pMS plasmids[15] encoding the sequence of Gb-H22(scFv) (fusion protein of granzyme B (Gb) and single chain H22) has already been described[16]. Via the integrated restriction sites Xbal/Blpl the encoding sequence for Gb was exchanged by the one for granzyme M. According to the same procedures the construction of Gm-Ki4(scFv) was performed on basis of the already published sequence for the single chain Ki4[17]. In a same manner all other constructs described here have been generated using basic molecular biological methods.

The specificity of the binding partners of the cytolytic fusion proteins are as follows: H22(scFv) is a humanized single chain specific to Fc gamma receptor I (CD64) whereas the murine Ki4(scFv) binds to CD30. As described above, the 72 kDa glycoprotein CD64 (FcγRI) is the mediator of endocytosis and phagocytosis, antibody-dependent cellular cytotoxicity and production of cytokines and superoxide. It is involved in inflammatory diseases and also over-expressed on the surface of leukemic cells. CD30 is a glycosylated type I transmembrane protein and belongs to the tumor necrosis factor receptor superfamily. It turned out to be a promising target for the treatment of Hodgkin lymphoma in previous studies (Schwab, Stein et al. 1982; Gruss, Pinto et al. 1996). RFT5(scFv) binds to CD25, a 55 kDa low affinity IL-2 receptor α which is efficiently induced upon T cell activation, not detectable on resting T cells, B cells or monocytes and is overexpressed on Hodgkin and Reed-Sternberg cells. It is also present in adult T cell leukemia, peripheral T cell leukemia/lymphomas, cutaneous T cell lymphoma, B cell non-Hodgkin's lymphomas, hairy cell leukemia, chronic lymphocytic leukemia, and acute myeloblastic leukemia[18]. 425(scFv) binds to EGFR, a cell-surface glycoprotein composed of a single polypeptide chain that binds the peptide Epidermal Growth Factor.

The pMS plasmid containing the cloning cassette for the fusion proteins including granzyme M and a single chain (here H22(scFv)) can be found in FIG. 1. FIGS. 18-22 display the nucleotide and amino acid sequences of the used single chains fused to granzyme M (FIGS. 19-22) and the granzyme M sequence alone (FIG. 18). The schematic structure of embodiments of the cytolytic fusion proteins according to the present disclosure is shown in FIG. 2. The abbreviations in FIG. 2 means the following: pMS-IV is the used vector system, IGK is the leader sequence to enable secretory expression, ECS is a sequence encoding an enterokinase site for the in vitro activation of Granzyme M, IVS/IRES is a synthetic intron/internal ribosome entry site.

Example 2

Cell Lines and Primary Cells

The used cell lines L540, L428, L1236 and HL60 and the expression cell line HEK293T (Graham et al., 1977) were kept in RPMI complex medium (RPMI 1640 plus Gluta-MAX-I) supplemented with 10% (v/v) FCS and 100 µg/ml penicillin and streptomycin (abbreviated as R10) at 37° C. and 5% $CO_2$. After transfection of HEK293T cells 100 µg/ml Zeocin was added for selection purposes.

L428 (ACC-197), L540 (ACC-72) and L1236 (ACC-530) are Hodgkin derived cell lines. L1236 is established from the peripheral blood of a 34-year-old man with Hodgkin lymphoma (mixed cellularity, stage IV, refractory, terminal, third relapse) in 1994, L428 is established from the pleural effusion of a 37-year-old woman with Hodgkin lymphoma (stage IVB, nodular sclerosis, refractory, terminal) in 1978 and L540 is established from the bone marrow of a 20-year-old woman with Hodgkin lymphoma (nodular sclerosis; stage IVB, pre-terminal stage).K562 (ACC-10) is established from the pleural effusion of a 53-year-old woman with chronic myeloid leukemia (CML) in blast crisis in 1970. The HL60 cell line is established from the peripheral blood of a 35-year-old woman with acute myeloid leukemia (AML FAB M2) in 1976.

Primary cells from CMML (chronic myelomonocytic leukemia) patients were obtained after informed consent and with the approval of the Clinical Research Ethics Board of the University of Aachen. Mononuclear cells were isolated from peripheral blood by density gradient centrifugation using Biocoll separating solution (Biochrom AG) and cultured in R10. For viability assays 200 U/ml Interferon γ was added for retaining activation of CD64 expression during cultivation.

Example 3

Detection of Serpin B9 in Tumor Cell Lines and Primary Tumor Cells Via Western Blot Analysis For the detection of endogenous Serpin B9 (also called PI9) expression within tumor cell lines or primary tumor cells from leukemic patients, $10^6$ cells were lysed within 50 µl lysis buffer (Phosphate buffered Saline (PBS) supplemented with 1% Triton X-100) for 30 minutes on ice. The cell extract was cleared via centrifugation and the protein concentration determined with Bradford reagent (BioRad). 40 µg of total soluble protein was loaded on an SDS gel for western blot analysis. After electroblotting onto nitrocellulose membranes and blocking with PBS supplemented with 0.05% Tween-20 and 2.5% milk powder, Serpin B9 was detected with anti-human PI9 (Santa Cruz, clone 7D8) and peroxidase-conjugated anti-mouse-IgG mAb (1:5.000, Sigma) and visualized by an enhanced chemiluminescence (ECL) system (BD BioScience) and LAS-3000 (Fujifilm).

Figure 13:
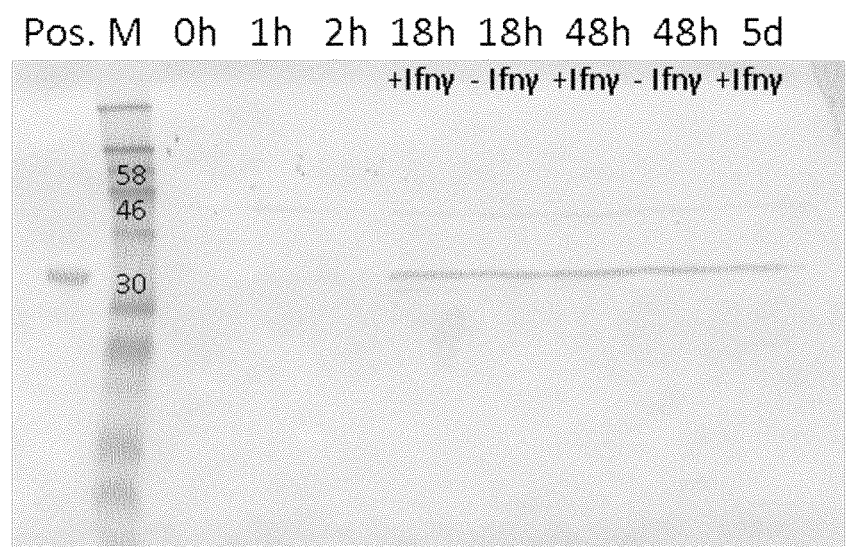
FIG. 13 shows the PI9 expression within primary CMML cells.
Figure 14:
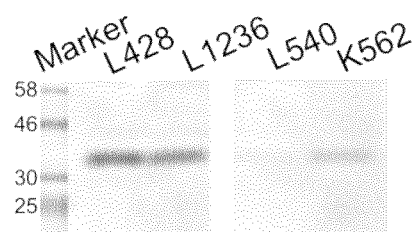
FIG. 14 shows the PI9 expression within different CD30$^+$ target cell lines and the results of viability assays of Gm-Ki4 (scFv) on L540cy cells.
Figure 14:
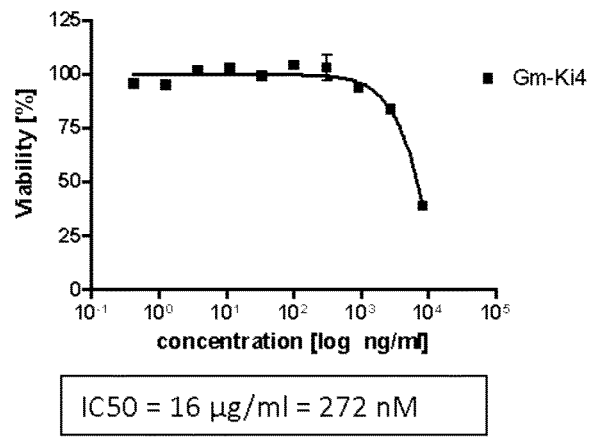

FIG. 14A shows the PI9 expression within the used cell lines L428, L1236, K562 and L540. HL60 are as L540 PI9 negative. FIG. 13 shows the PI9 expression within CMML patient material.

Example 4

Protein Expression in Mammalian Cells and Purification

HEK293T cells were used as expression cell line. The cells were transfected with 1 µg DNA according to the manufacturer's instructions using RotiFect (Roth). The used pMS plasmid encodes for the bicistronic EGFP reporter so that expression of the target protein could be verified by green fluorescence via fluorescence microscopy.

The secreted protein could be purified from the cell culture supernatant via Immobilized Metal-ion Affinity Chromatography (IMAC) and Fast Performance Liquid Chromatography (FPLC). The cleared supernatant was supplemented with 10 mM imidazole and loaded to an XK16/20 column (Amersham/GE Healthcare) containing 8 ml Sepharose 6 Fast Flow resin (Clontech/Takara). The used buffers such as incubation, washing and elution buffer were described before[15]. The eluted protein was re-buffered into 20 mM Tris, pH 7.4, 250 mM NaCl, concentrated, aliquoted and stored at −80° C. For activation prior to use Enterokinase was added to the protein (0.02 U/µg) with 2 mM $CaCl_2$ for 16 h incubation at 23° C. The purified proteins or cell extracts were analysed via SDS-PAGE under reducing conditions and Coomassie staining. Western blots were performed according to standard techniques. The protein concentration was calculated from Coomassie stained SDS gels using different concentrations of bovine serumalbumin as standard and AIDA Image Analyzer Software.

FIGS. 3A, 4A, 5A and 6 show Coomassie stained SDS gels and corresponding western blots of the purified proteins. Detection in western blots was done with anti-human granzyme M (Abnova) and an alkaline phosphatase-conjugated anti-mouse-IgG mAb (1:5.000; Sigma) followed by staining with Tris-HCl (pH 8.0) and 0.2 mg/ml naphtol-AS-Bi-phosphate (Sigma, Germany) supplemented with 1 mg/ml Fast-Red (Serva) or a peroxidase-conjugated anti-mouse-IgG mAb (GAM-PO, 1:5.000, Sigma) for chemiluminescence detection (reagents from BD Thermoscientific and detection with LAS-3000 (Fujifilm)).

Example 5

Determination of Granzyme M Activity Via Complex Formation with PI9

The complex formation between recombinant Serpin B9 (expressed and purified as described before[20]) and Gm-H22 (scFv), Gm-Ki4(scFv) or Gm-425(scFv) took place at 25° C. in assay buffer containing 100 mM HEPES, pH 7.4, 200 mM NaCl, 0.01% Tween 20 and 1 mM DTT in a 1:3 molar ratio. After 24 hours the reaction mixture was analyzed via SDS-PAGE and western blotting according to standard techniques using anti-human PI9 (clone 7D8, Santa Cruz) and GAM-PO (Sigma) as second antibody. The chemiluminescent signal was monitored with LAS-3000 (Fujifilm).

Figure 3:
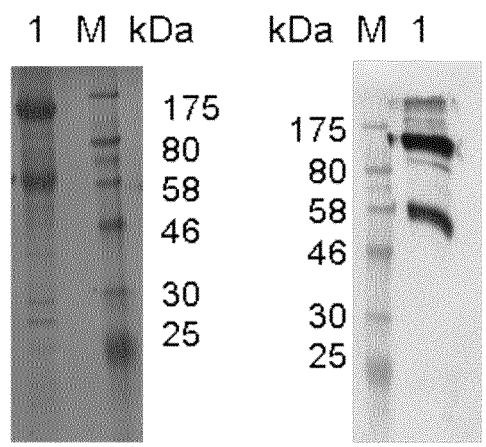
FIG. 3 shows the purified Gm-H22(scFv) in a Coomassie stained SDS-PAGE gel and Western Blot (A) and the enzymatic activity of granzyme M towards Serpin B9 in a Western Blot (B).
Figure 3:
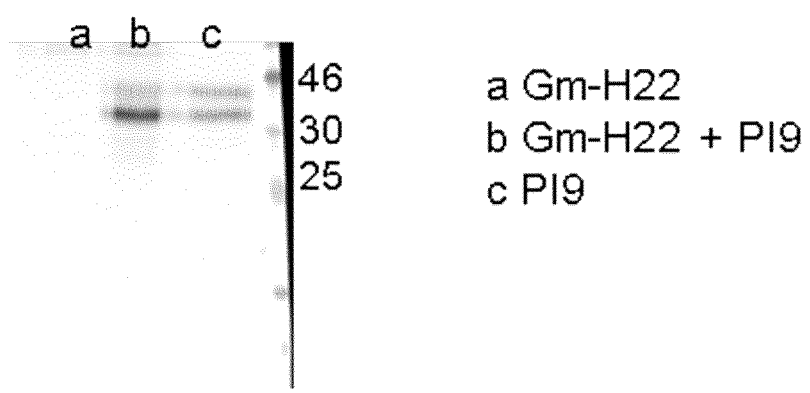
Figure 4:
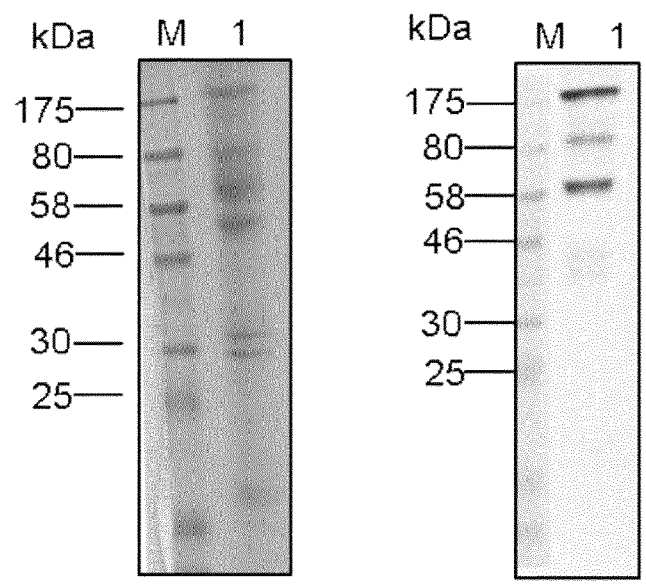
FIG. 4 shows the purified Gm-Ki4(scFv) in a Coomassie stained SDS-PAGE gel and Western Blot (A) and the enzymatic activity of granzyme M towards Serpin B9 in a Western Blot (B).
Figure 4:
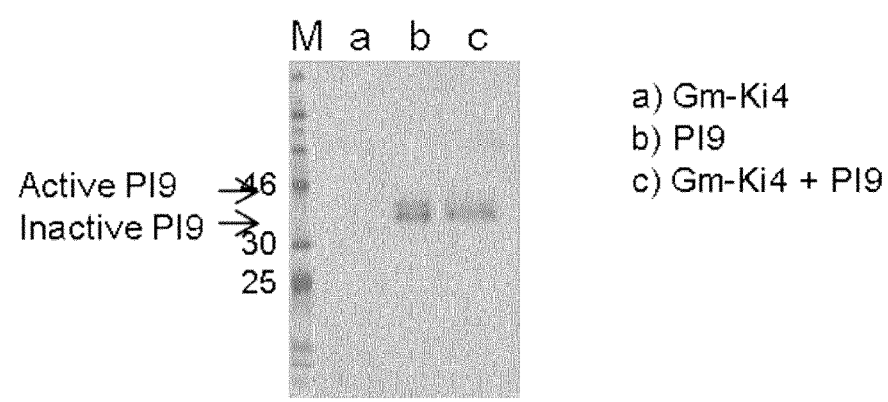
Figure 5:
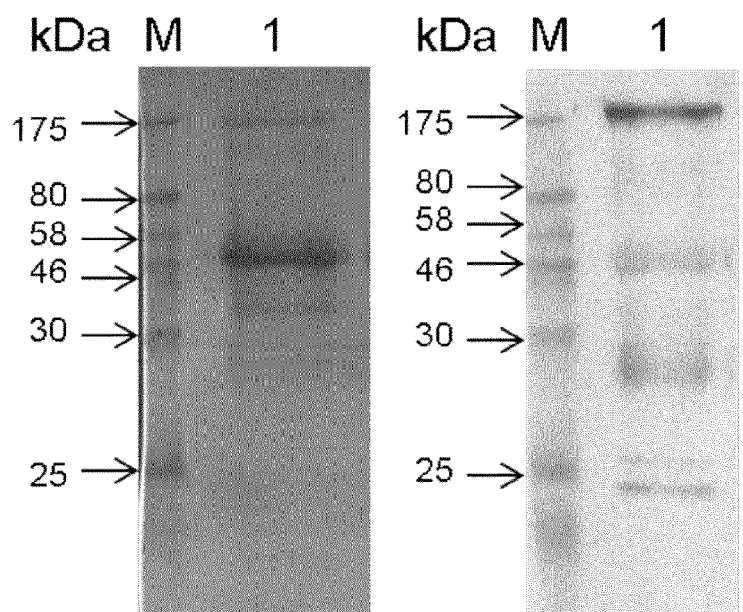
FIG. 5 shows the purified Gm-425(scFv) in a Coomassie stained SDS-PAGE gel and Western Blot (A) and the enzymatic activity of granzyme M towards Serpin B9 in a Western Blot (B).
Figure 5:
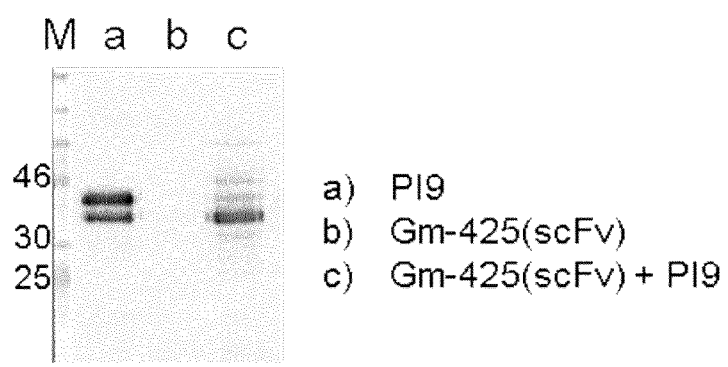
Figure 6:
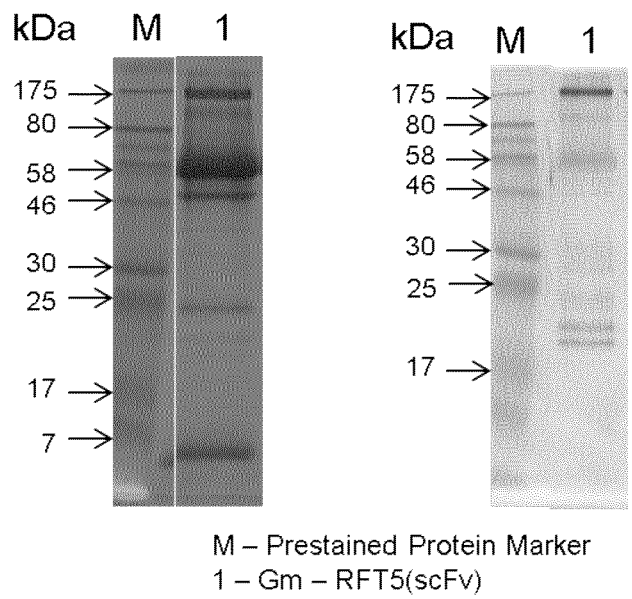
FIG. 6 shows the purified Gm-RFT5(scFv) in a Coomassie stained SDS-PAGE gel and Western Blot.
Figure 6:
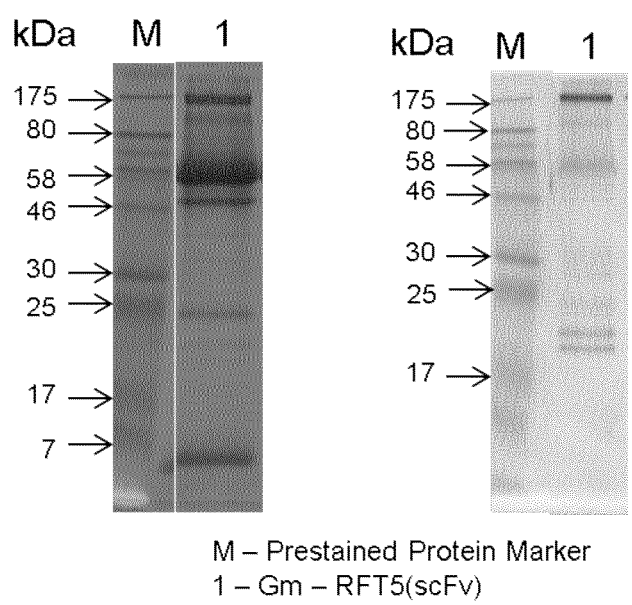

FIGS. 3B, 4B and 5B show the resulting western blots with cleaved SerpinB9 after incubation with the granzyme M constructs. All constructs are active according to their enzymatic activity.

Example 6

Binding Analysis

The binding of the granzyme M constructs to the target cell lines was evaluated by flow cytometry. $4*10^5$ cells were washed with PBS and incubated with 1 µg purified protein in 100 µl PBS for 30 minutes on ice. After 2 wash cycles (Dade Serocent) cells were incubated with anti-His Alexa 488 for 30 min on ice in the dark. Unbound antibodies were removed by washing with PBS. Specific binding was determined with the help of FACSCalibur flow cytometer (Becton Dickinson).

Figure 7:
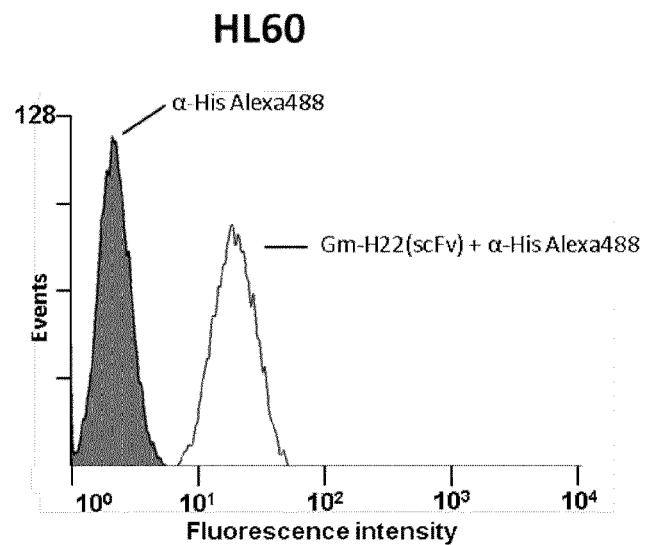
FIG. 7 shows the binding analysis of Gm-H22(scFv) to CD64$^+$ HL60 and the negative control L428.
Figure 7:
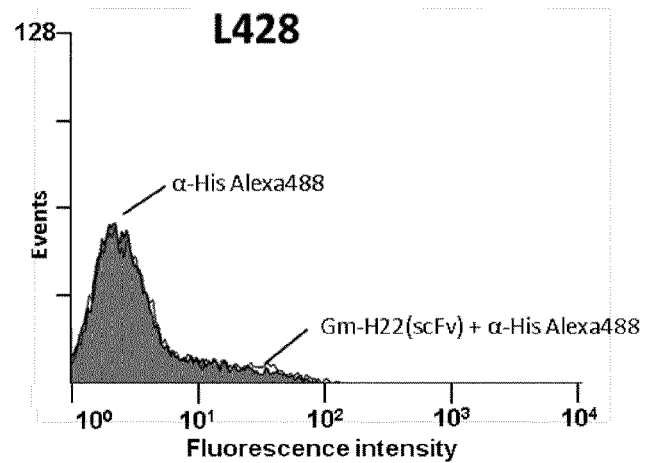
Figure 8:
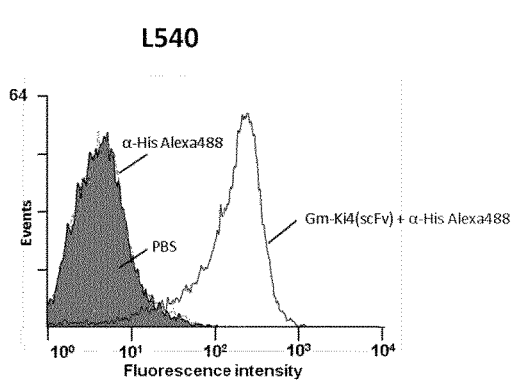
FIG. 8 shows the binding analysis of Gm-Ki4(scFv) to CD30$^+$ cell lines and the negative control H L60.
Figure 8:
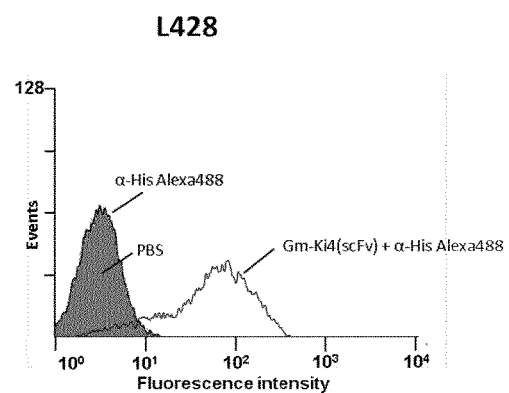
Figure 8:
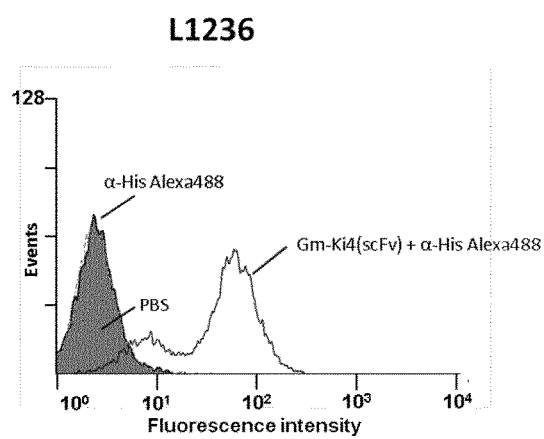
Figure 8:
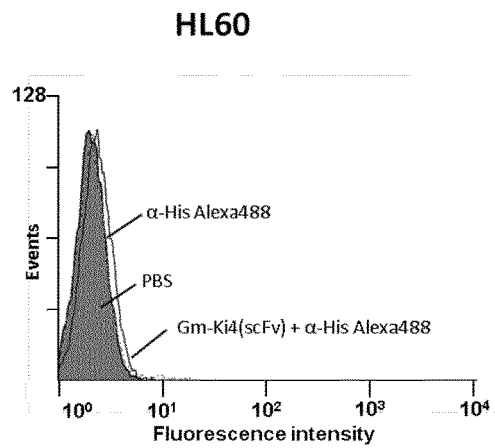
Figure 9:
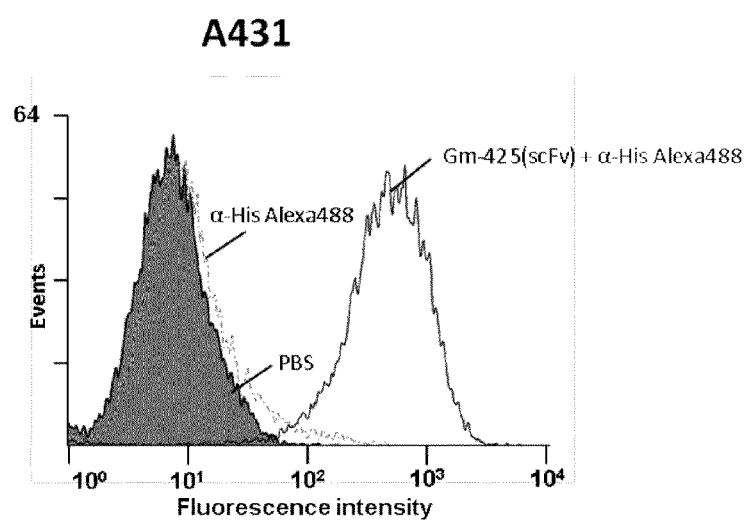
FIG. 9 shows the binding analysis of Gm-425(scFv) to EGFR$^+$ A431 and the negative control L540.
Figure 9:
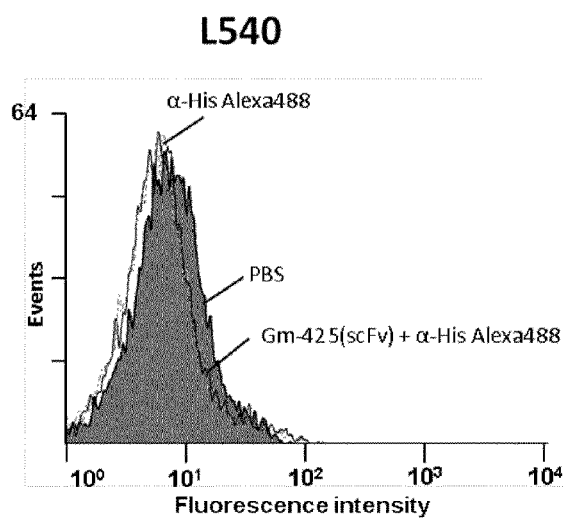

FIG. 7-9 shows results of the binding analysis. For each construct a negative control not expressing the corresponding receptor is shown (L428 for Gm-H22(scFv), HL60 for Gm-Ki4(scFv) and L540 for Gm-425(scFv)). All constructs bind specifically to their target cell lines and no unspecific binding was detected.

Example 7

Apoptosis Assay

Apoptosis was documented via AnnexinV/Propidium iodide (PI) staining. $2*10^5$ cell/ml were incubated at 37° C. and 5% $CO_2$ with cytolytic fusion protein in 12 well plates. After incubation, cells were washed in PBS and the pellet was re-suspended in 450 µl cell-free culture supernatant from HEK293T cells expressing AnnexinV-labeled green fluorescent protein supplemented with 10× AnnexinV binding buffer (100 mM HEPES, pH 7.5, 1.5 M NaCl, 50 mM KCl and 20 mM $CaCl_2$) as well as 5 µg/ml PI. The incubation took place for 20 minutes on ice in the dark and the analysis was done via flow cytometric measurements. FL1 channel (X axis) detects GFP fluorescence whereby FL3 channel (Y axis) determines PI. Explanation of corresponding dotplots: quadrant upper right=late apoptotic cells (AnnexinV and PI positive), quadrant upper left=necrotic cells (AnnexinV negative and PI positive), quadrant lower right=early apoptotic cells (AnnexinV positive and PI negative), quadrant lower left=viable cells (AnnexinV and PI negative).

Figure 11:
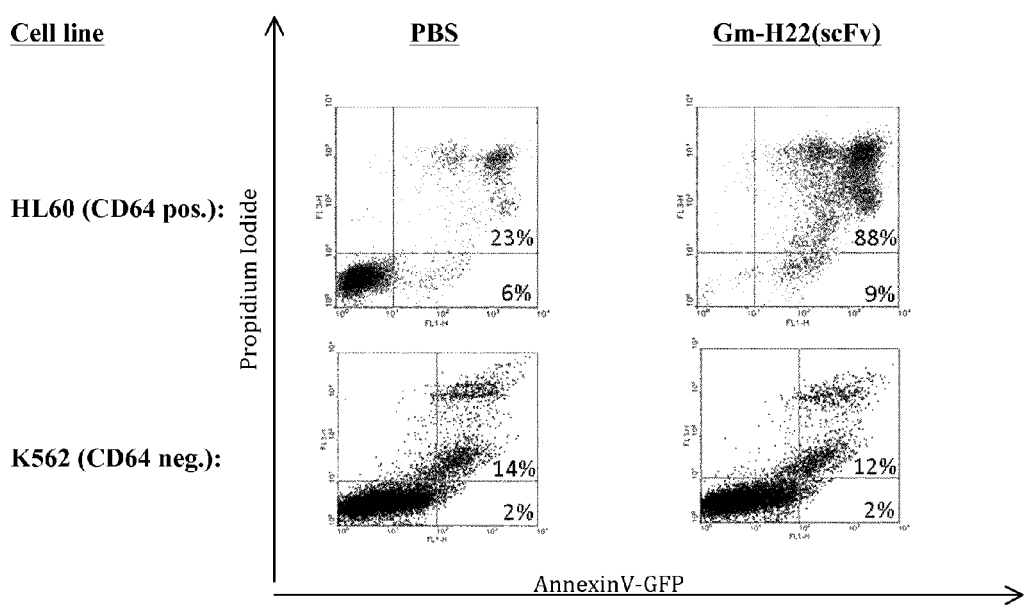
FIG. 11 shows the results of apoptosis assays of Gm-H22 (scFv) on HL60 cell line and negative control.

FIG. 11 shows results of Annexin V assay with Gm-H22 (scFv) on CD64 positive HL60 and CD64 negative K562. It can be seen that the cytotoxic effect is induced by apoptosis and that it is specific. Cells were incubated with 66 nM protein for 48 hours.

Figure 15:
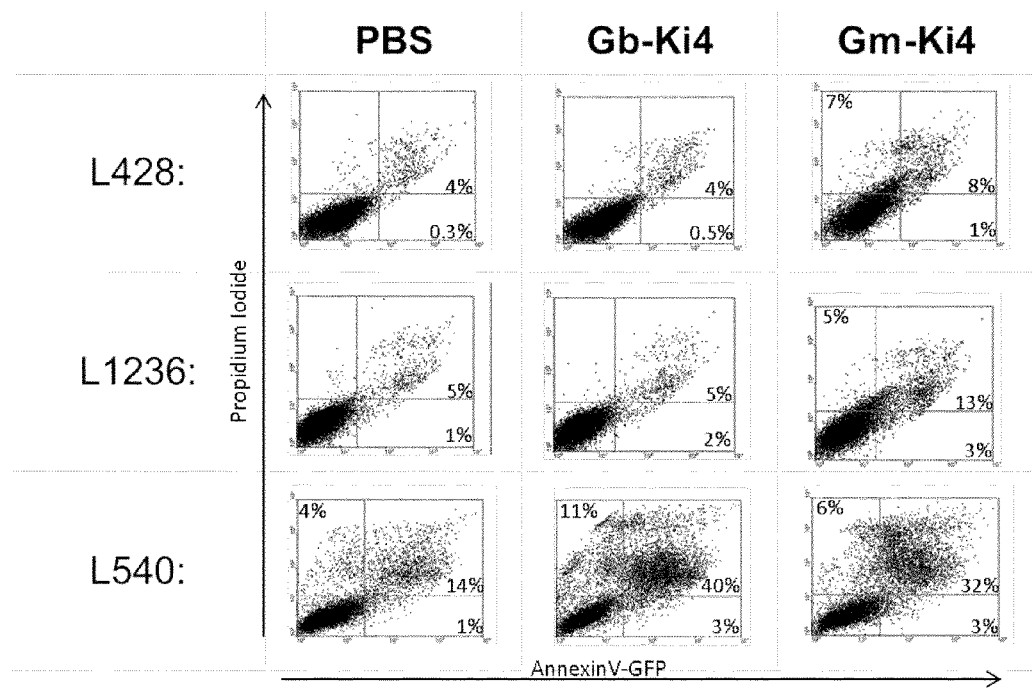
FIG. 15 shows the results of apoptosis assays of Gm-Ki4 (scFv) on PI9$^+$ and PI9$^-$ cells.
Figure 15:
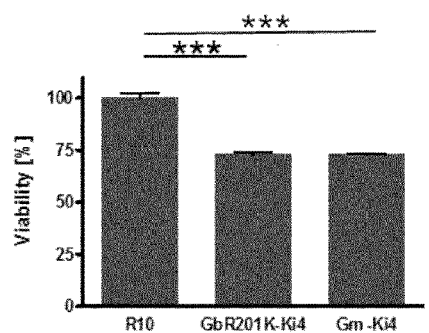

FIG. 15A presents apoptotic effects of Gm-Ki4(scFv) on PI9 positive L428 and L1236 cell lines and PI9 negative L540 cell line. Analysis was done after incubation of the cells with 11 nM or 33 nM cytolytic fusion protein respectively for 48 hours. Comparison to Gb-Ki4(scFv) is shown which does not induce apoptosis on PI9 positive cells in contrast to Gm-Ki4(scFv).

Figure 17:
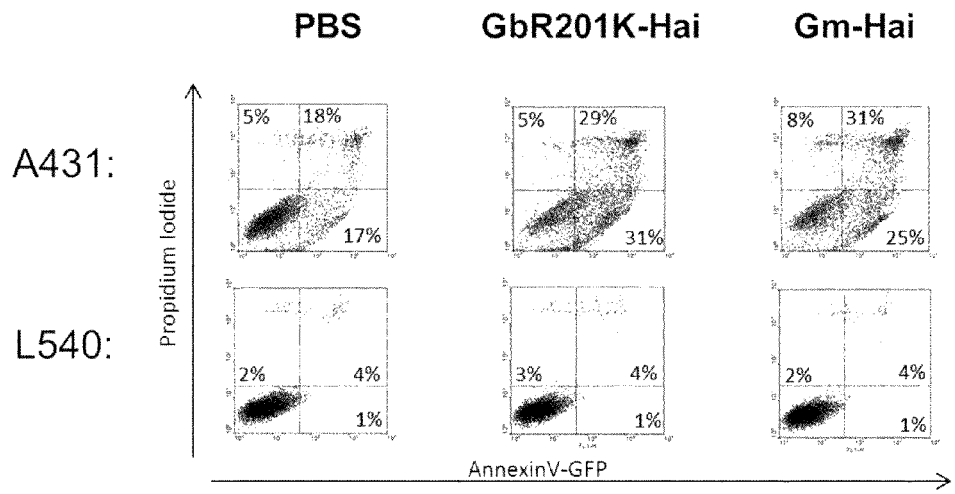
FIG. 17 shows the results of viability and apoptosis assays of Gm-425(scFv) on A431 target cell line and negative control L540.
Figure 17:
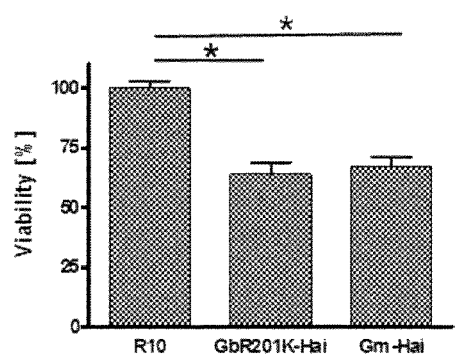
Figure 17:
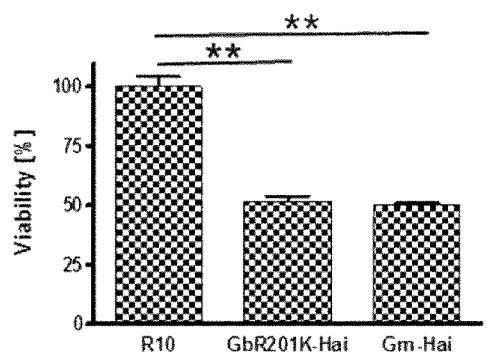

FIG. 17A-B shows the results of an AnnexinV assay after incubation of PI9 negative A431 cell line with 100 nM Gm-425(scFv) compared to 100 nM GbR201K-425(scFv). As negative control L540 cells were incubated with the same amount of protein. In FIG. 17B apoptotic effects were converted to viability and buffer control was set to 100%.

Example 8

Viability Assay

Dose-depending cytotoxic effects were monitored using the ability of metabolic active cells to reduce the tetrazolium salt XTT to orange colored compounds of formazan. The intensity of light was measured by a microplate reader and is directly proportional to the number of living cells. 5000 cells for cell lines and 20.000 cells for primary cells were plated in 100 µl of R10 in 96-well plates either in 1:5 or 1:3 serial dilutions. In another approach single protein concentrations of 11 or 21 nM (if not otherwise indicated) of the respective cytolytic fusion protein was added to $3*10^5$ cells in 12-well plates and incubated at 37° C. and 5% $CO_2$. After 48 hours incubation, 100 µl of the cell suspension were transferred into 96-well plates and 50 µl XTT was added. Read out was done at 450 nm with reference wavelength of 650 nm. The same set-up was used for dose-depending measurements with the L540 cell line.

Figure 10:
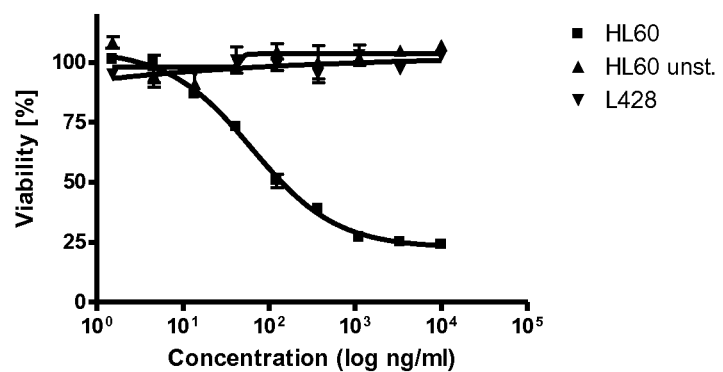
FIG. 10 shows the results of viability assay of Gm-H22 (scFv) on HL60 cell line and negative controls.
Figure 12:
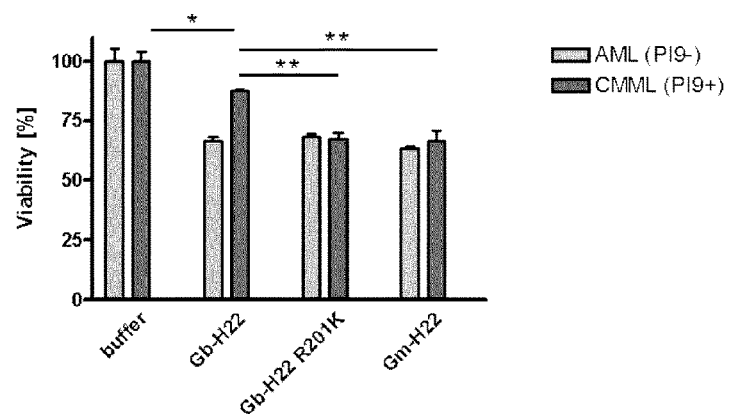
FIG. 12 shows the results of viability assay on Gm-H22 (scFv) on primary CD64$^+$ cells.
Figure 12:
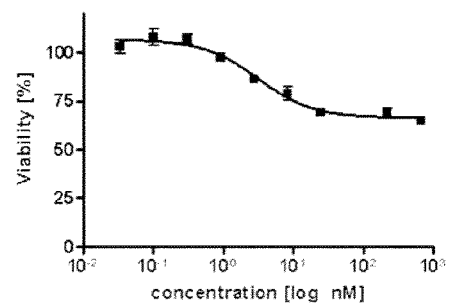
Figure 12:
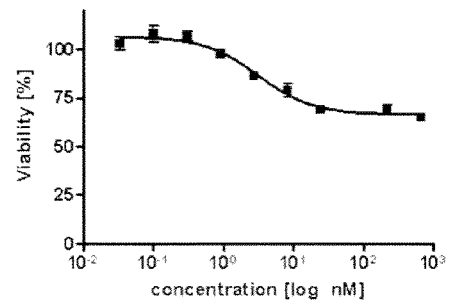

FIG. 10 shows dose-depending curves detected via XTT for Gm-H22(scFv) on Interferon γ stimulated and non-stimulated HL60 cells and L428 cell line (latter two used as negative controls). Specific toxicity on stimulated HL60 cells was confirmed with an $IC_{50}$ of 1.2 nM. FIG. 12A displays toxic effect of the construct on primary AML or CMML cells (tested to be PI9 positive as shown in FIG. 13) whereby single cytolytic fusion protein concentrations of 21 nM were added to the cells and incubated for 48 hours. For comparison the results of Gb-H22(ScFv) and its mutant Gb-H22(scFv) R201K are shown as well. FIG. 12B shows dose-dependent cytotoxicity of Gm-H22(scFv) on primary AML cells.

FIG. 15B presents viability measurement after incubation of PI9 positive L428 cells with Gm-Ki4(scFv) and Gb-Ki4 (scFv) R201K as control. Analysis was done after incubation of the cells with 11 nM cytolytic fusion protein for 48 hours. Apoptosis is induced by both Gm-Ki4(scFv) and the control Gb-Ki4(scFv) R201K whereby the wildtype Gb-Ki4(scFv) does not induce apoptosis. Thus granzyme M fusion protein can trigger cell death in the presence of SerpinB9 that is associated with therapy-resistance (2011_Ray, 2012_Soriano).

FIG. 14B shows the dose-depending toxicity curve for Gm-Ki4(scFv) on L540 cells with an $IC_{50}$ of 272 nM. FIG. 16 presents the viability of PI9 positive K562 cells after incubation with 11 nM Gb-Ki(scFv), Gb-Ki4(scFv) R201K and co-incubation of Gb-Ki4(scFv) R201K and Gm-Ki4 (scFv) whereby Gm-Ki4(scFv) was added 24 hours prior to Gb-Ki4(scFv) R201K. An additive effect by addition of Gm-Ki4(scFv) was confirmed. The granzyme B variant comprised in Gb-Ki4(scFv) R201K has a substitution at position 201 of the of wildtype human granzyme B and showing increased apoptotic activity compared to wildtype granzyme B and reduced sensitivity to activity-inhibiting substances.

FIG. 17C shows the results of a viability assay evaluated via XTT after incubation of PI9 negative A431 cell line with 100 nM Gm-425(scFv) compared to 100 nM Gb-425(scFv) R201K for 72 hours. Both constructs induce apoptosis within the target cells to the same extent.

REFERENCES

1 Schnell, R. et al. Clinical evaluation of ricin A-chain immunotoxins in patients with Hodgkin's lymphoma. Annals of oncology: official journal of the European Society for Medical Oncology/ESMO 14, 729-736 (2003).
2 Pirker, R., FitzGerald, D. J., Willingham, M. C. & Pastan, I. Enhancement of the activity of immunotoxins made with either ricin A chain or *Pseudomonas* exotoxin in human ovarian and epidermoid carcinoma cell lines. Cancer research 48, 3919-3923 (1988).
3 Pai, L. H. & Pastan, I. Clinical trials with *Pseudomonas* exotoxin immunotoxins. Current topics in microbiology and immunology 234, 83-96 (1998).
4 Mathew, M. & Verma, R. S. Humanized immunotoxins: a new generation of immunotoxins for targeted cancer therapy. Cancer science 100, 1359-1365, doi:10.1111/j.1349-7006.2009.01192.x (2009).
5 Smyth, M. J., O'Connor, M. D., Trapani, J. A., Kershaw, M. H. & Brinkworth, R. I. A novel substrate-binding pocket interaction restricts the specificity of the human NK cell-specific serine protease, Met-ase-1. J Immunol 156, 4174-4181 (1996).

6. Bade, B. et al. Differential expression of the granzymes A, K and M and perforin in human peripheral blood lymphocytes. Int Immunol 17, 1419-1428, doi:DOI 10.1093/intimm/dxh320 (2005).
7. Sayers, T. J. et al. The restricted expression of granzyme M in human lymphocytes. J Immunol 166, 765-771 (2001).
8. Bovenschen, N. et al. NK cell protease granzyme M targets alpha-tubulin and disorganizes the microtubule network. J Immunol 180, 8184-8191 (2008).
9. Lu, H. et al. granzyme M directly cleaves inhibitor of caspase-activated DNase (CAD) to unleash CAD leading to DNA fragmentation. J Immunol 177, 1171-1178 (2006).
10. Hu, D. et al. Cleavage of survivin by granzyme M triggers degradation of the survivin-X-linked inhibitor of apoptosis protein (XIAP) complex to free caspase activity leading to cytolysis of target tumor cells. J Biol Chem 285, 18326-18335, doi:10.1074/jbc.M109.083170 (2010).
11. Hua, G., Zhang, Q. & Fan, Z. Heat shock protein 75 (TRAP1) antagonizes reactive oxygen species generation and protects cells from Granzyme M-mediated apoptosis. J Biol Chem 282, 20553-20560, doi:10.1074/jbc.M703196200 (2007).
12. Mahrus, S., Kisiel, W. & Craik, C. S. granzyme M is a regulatory protease that inactivates proteinase inhibitor 9, an endogenous inhibitor of granzyme B. J Biol Chem 279, 54275-54282, doi:M411482200 [pii]10.1074/jbc.M411482200 (2004).
13. Bladergroen, B. A. et al. Expression of the granzyme B inhibitor, protease inhibitor 9, by tumor cells in patients with non-Hodgkin and Hodgkin lymphoma: a novel protective mechanism for tumor cells to circumvent the immune system? Blood 99, 232-237 (2002).
14. ten Berge, R. L. et al. Expression levels of apoptosis-related proteins predict clinical outcome in anaplastic large cell lymphoma. Blood 99, 4540-4546 (2002).
15. Stocker, M. et al. Secretion of functional anti-CD30-angiogenin immunotoxins into the supernatant of transfected 293T-cells. Protein expression and purification 28, 211-219 (2003).
16. Stahnke, B. et al. granzyme B-H22(scFv), a human immunotoxin targeting CD64 in acute myeloid leukemia of monocytic subtypes. Molecular Cancer Therapeutics 7, 2924-2932, doi:Doi 10.1158/1535-7163.Mct-08-0554 (2008).
17. Klimka, A. et al. Human anti-CD30 recombinant antibodies by guided phage antibody selection using cell panning. British journal of cancer 83, 252-260, doi:10.1054/bjoc.2000.1226 (2000).
18. Kreitman, R. J. & Pastan, I. Recombinant toxins. Advances in pharmacology 28, 193-219 (1994).
19. von Kalle, C. et al. Growth of Hodgkin cell lines in severely combined immunodeficient mice. Int J Cancer 52, 887-891 (1992).
20. Losasso, V., Schiffer, S., Barth, S. & Carloni, P. Design of human granzyme B variants resistant to serpin B9. Proteins, doi:10.1002/prot.24133 (2012).

The invention claimed is:

1. A cytolytic fusion protein suitable to induce apoptosis in a target cell comprising at least a first polypeptide comprising a binding structure, wherein the binding structure is an antibody or an antibody binding fragment comprising the amino acid sequence of SEQ ID NO. 8 or SEQ ID NO. 10, which allows binding of the fusion protein to a specific target structure on the surface of a diseased cell, wherein the specific target structure is CD25 or EGFR, and at least a second polypeptide comprising a cytolytic serine protease, wherein the serine protease is granzyme M.

2. The cytolytic fusion protein according to claim 1, wherein the diseased cell is a cancer cell.

3. The cytolytic fusion protein according to claim 1, wherein the antibody or antibody fragment is selected from the group consisting of an Fab, a scFv, a bis scFv, an Fab2, an Fab3, a minibody, a diabody, a triabody, a tetrabody, and a tandab.

4. The cytolytic fusion protein according to claim 1, wherein the cytolytic serine protease comprises the amino acid sequence of SEQ ID NO. 2.

5. The cytolytic fusion protein according to claim 1, wherein the cytolytic fusion protein comprises the amino acid sequence of SEQ ID NO. 8.

6. The cytolytic fusion protein according to claim 1, further comprising one or more further polypeptide(s) selected from the group consisting of a leader sequence capable of controlling protein biosynthesis, a protein tag, a translocation domain amphiphatic sequence capable of translocating the fusion protein into the cytosol of the target cell, and a synthetic pro-serine protease amphiphatic sequence capable of intracellular activation of the serine protease.

7. The cytolytic fusion protein according to claim 1, wherein the cytolytic fusion protein further comprises a leader sequence for secretory expression, an enterokinase cleavage site, and a HIS tag.

8. A nucleic acid molecule encoding the cytolytic fusion protein according to claim 1.

9. A vector comprising the nucleic acid molecule of claim 8.

10. A host cell transformed with the vector of claim 9.

11. A method for preparing a cytolytic fusion protein, which comprises culturing the host cell of claim 10 under conditions for expressing the protein encoded by the nucleic acid molecule; and isolating the cytolytic fusion protein from the culture.

12. A pharmaceutical composition comprising the cytolytic fusion protein according to claim 1.

13. The pharmaceutical composition according to claim 12, wherein the composition further comprises a second cytolytic fusion protein suitable to induce apoptosis in a target cell comprising at least a second binding structure embodied as an antibody or an antibody fragment, which allows binding of the second fusion protein to a second specific target structure on the surface of a diseased cell, wherein the second specific structure is selected from the group consisting of CD64, CD25, CD30, and EGFR and at least a second polypeptide comprising a cytolytic serine protease, wherein the serine protease is granzyme B.

14. The pharmaceutical composition according to claim 13, wherein the second binding structure comprises an amino acid sequence selected from the group consisting of SEQ ID NO. 4, SEQ ID NO. 6, SEQ ID NO. 8, and SEQ ID NO. 10, further wherein the binding structure and second binding structure bind different specific target structures on the surface of a same diseased cell.

15. A cytolytic fusion protein suitable to induce apoptosis in a target cell comprising at least a first polypeptide comprising a binding structure comprising the amino acid sequence of SEQ ID NO. 6, which allows binding of the fusion protein to CD30 on the surface of a diseased cell, and at least a second polypeptide comprising a cytolytic serine protease, wherein the serine protease is granzyme M.

16. A cytolytic fusion protein suitable to induce apoptosis in a target cell comprising at least a first polypeptide comprising a binding structure comprising the amino acid sequence of SEQ ID NO. 4, which allows binding of the fusion protein to CD64 on the surface of a diseased cell, and at least a second polypeptide comprising a cytolytic serine protease, wherein the serine protease is granzyme M.

17. The cytolytic fusion protein according to claim 15, wherein the first polypeptide is selected from the group consisting of an Fab, a scFv, a bis scFv, an Fab2, an Fab3, a minibody, a diabody, a triabody, a tetrabody, and a tandab.

18. The cytolytic fusion protein according to claim 16, wherein the first polypeptide is selected from the group consisting of an Fab, a scFv, a bis scFv, an Fab2,an Fab3, a minibody, a diabody, a triabody, a tetrabody, and a tandab.

19. The cytolytic fusion protein according to claim 1, wherein the amino acid comprises SEQ ID NO. 10.

* * * * *

SEQUENCE LISTING

```
<160> NUMBER OF SEQ ID NOS: 10

<210> SEQ ID NO 1
<211> LENGTH: 696
<212> TYPE: DNA
<213> ORGANISM: Artificial Sequence
<220> FEATURE:
<223> OTHER INFORMATION: wt human granzyme M

<400> SEQUENCE: 1
atcatcgggg gccgggaggt gatcccccac tcgcgcccgt acatggcctc actgcagaga      60
aatggctccc acctgtgcgg gggtgtcctg gtgcacccaa agtgggtgct gacggctgcc     120
cactgcctgg cccagcggat ggcccagctg aggctggtgc tggggctcca cacctggac     180 agccccggtc tcaccttcca catcaaggca gccatccagc accctcgcta caagcccgtc     240
cctgccctgg agaacgacct cgcgctgctt cagctggacg ggaaagtgaa gcccagccgg     300
accatccggc cgttggccct gcccagtaag cgccaggtgg tggcagcagg gactcggtgc     360
agcatggccg gctgggggct gacccaccag ggcgggcgc tgtcccgggt gctgcgggag     420 ctggaccctcc aagtgctgga cacccgcatg tgtaacaaca gccgcttctg gaacggcagc     480
ctctccccca gcatggtctg cctggcggcc gactccaagg accaggctcc ctgcaagggt     540
gactcgggcg ggcccctggt gtgtggcaaa ggccgggtgt tggccggagt cctgtccttc     600
agctccaggg tctgcactga catcttcaag cctcccgtgg ccaccgctgt ggcgccttac     660
gtgtcctgga tcaggaaggt caccggccga tcggcc                               696

<210> SEQ ID NO 2
<211> LENGTH: 232
<212> TYPE: PRT
<213> ORGANISM: Artificial Sequence
```

<220> FEATURE:
<223> OTHER INFORMATION: wt human granzyme M

<400> SEQUENCE: 2

```
Ile Ile Gly Gly Arg Glu Val Ile Pro His Ser Arg Pro Tyr Met Ala
1               5                   10                  15

Ser Leu Gln Arg Asn Gly Ser His Leu Cys Gly Gly Val Leu Val His
            20                  25                  30

Pro Lys Trp Val Leu Thr Ala Ala His Cys Leu Ala Gln Arg Met Ala
        35                  40                  45

Gln Leu Arg Leu Val Leu Gly Leu His Thr Leu Asp Ser Pro Gly Leu
    50                  55                  60

Thr Phe His Ile Lys Ala Ala Ile Gln His Pro Arg Tyr Lys Pro Val
65                  70                  75                  80

Pro Ala Leu Glu Asn Asp Leu Ala Leu Leu Gln Leu Asp Gly Lys Val
                85                  90                  95

Lys Pro Ser Arg Thr Ile Arg Pro Leu Ala Leu Pro Ser Lys Arg Gln
            100                 105                 110

Val Val Ala Ala Gly Thr Arg Cys Ser Met Ala Gly Trp Gly Leu Thr
        115                 120                 125

His Gln Gly Gly Arg Leu Ser Arg Val Leu Arg Glu Leu Asp Leu Gln
    130                 135                 140

Val Leu Asp Thr Arg Met Cys Asn Asn Ser Arg Phe Trp Asn Gly Ser
145                 150                 155                 160

Leu Ser Pro Ser Met Val Cys Leu Ala Ala Asp Ser Lys Asp Gln Ala
                165                 170                 175

Pro Cys Lys Gly Asp Ser Gly Gly Pro Leu Val Cys Gly Lys Gly Arg
            180                 185                 190

Val Leu Ala Gly Val Leu Ser Phe Ser Arg Val Cys Thr Asp Ile
        195                 200                 205

Phe Lys Pro Pro Val Ala Thr Ala Val Ala Pro Tyr Val Ser Trp Ile
    210                 215                 220

Arg Lys Val Thr Gly Arg Ser Ala
225                 230
```

<210> SEQ ID NO 3
<211> LENGTH: 1476
<212> TYPE: DNA
<213> ORGANISM: Artificial Sequence
<220> FEATURE:
<223> OTHER INFORMATION: Gm-H22 (scFv)

<400> SEQUENCE: 3

```
atcatcgggg gccgggaggt gatcccccac tcgcgcccgt acatggcctc actgcagaga      60
aatggctccc acctgtgcgg gggtgtcctg gtgcacccaa agtgggtgct gacggctgcc     120
cactgcctgg cccagcggat ggcccagctg aggctggtgc tggggctcca caccctggac     180
agccccggtc tcaccttcca catcaaggca gccatccagc accctcgcta caagcccgtc     240
cctgccctgg agaacgacct cgcgctgctt cagctggacg ggaaagtgaa gcccagccgg     300
accatccggc cgttggccct gcccagtaag cgccaggtgg tggcagcagg gactcggtgc     360
agcatggccg gctgggggct gacccaccag ggcgggcgcc tgtcccgggt gctgcgggag     420
ctggacctcc aagtgctgga cacccgcatg tgtaacaaca gccgcttctg gaacggcagc     480
ctctccccca gcatggtctg cctggcggcc gactccaagg accaggctcc ctgcaagggt     540
gactcgggcg ggcccctggt gtgtggcaaa ggccgggtgt tggccggagt cctgtccttc     600
```

```
agctccaggg tctgcactga catcttcaag cctcccgtgg ccaccgctgt ggcgccttac    660
gtgtcctgga tcaggaaggt caccggccga tcggccgctg agcacgaagg tgacgcggcc    720
cagccggcca tggcccaggt gcagctggtg gagagcggtg gaggtgttgt gcaacctggc    780
cggtccctgc gcctgtcctg ctcctcgtct ggcttcattt tcagtgacaa ttacatgtat    840
tgggtgagac aggcacctgg aaaaggtctt gagtgggttg caaccattag tgatggtggt    900
agttacaccc tactatccaga cagtgtgaag ggaagattta caatatcgag agacaacagc    960
aagaacacat tgttcctgca aatggacagc ctgagacccg aagacaccgg ggtctatttt   1020
tgtgcaagag gctactatag gtacgagggg gctatggact actggggcca agggaccccg   1080
gtcaccgtga gctcaggagg tggcggctcc ggaggtggag gcagcggagg gggcggatcc   1140
gacatccagc tgacccagag cccaagcagc ctgagcgcca gcgtgggtga cagagtgacc   1200
atcacctgta gtccagtca agtgttttta tacagttcaa atcagaagaa ctacttggcc   1260
tggtaccagc agaagccagg taaggctcca aagctgctga tctactgggc atccactagg   1320
gaatctggtg tgccaagcag attcagcggt agcggtagcg gtaccgactt caccttcacc   1380
atcagcagcc tccagccaga ggacatcgcc acctactact gccatcaata cctctcctcg   1440
tggacgttcg gccaagggac caagctggag atcaaa                              1476

<210> SEQ ID NO 4
<211> LENGTH: 492
<212> TYPE: PRT
<213> ORGANISM: Artificial Sequence
<220> FEATURE:
<223> OTHER INFORMATION: Gm-H22 (scFv)

<400> SEQUENCE: 4

Ile Ile Gly Gly Arg Glu Val Ile Pro His Ser Arg Pro Tyr Met Ala
1               5                   10                  15

Ser Leu Gln Arg Asn Gly Ser His Leu Cys Gly Gly Val Leu Val His
            20                  25                  30

Pro Lys Trp Val Leu Thr Ala Ala His Cys Leu Ala Gln Arg Met Ala
        35                  40                  45

Gln Leu Arg Leu Val Leu Gly Leu His Thr Leu Asp Ser Pro Gly Leu
    50                  55                  60

Thr Phe His Ile Lys Ala Ala Ile Gln His Pro Arg Tyr Lys Pro Val
65                  70                  75                  80

Pro Ala Leu Glu Asn Asp Leu Ala Leu Leu Gln Leu Asp Gly Lys Val
                85                  90                  95

Lys Pro Ser Arg Thr Ile Arg Pro Leu Ala Leu Pro Ser Lys Arg Gln
            100                 105                 110

Val Val Ala Ala Gly Thr Arg Cys Ser Met Ala Gly Trp Gly Leu Thr
        115                 120                 125

His Gln Gly Gly Arg Leu Ser Arg Val Leu Arg Glu Leu Asp Leu Gln
    130                 135                 140

Val Leu Asp Thr Arg Met Cys Asn Asn Ser Arg Phe Trp Asn Gly Ser
145                 150                 155                 160

Leu Ser Pro Ser Met Val Cys Leu Ala Ala Asp Ser Lys Asp Gln Ala
                165                 170                 175

Pro Cys Lys Gly Asp Ser Gly Gly Pro Leu Val Cys Gly Lys Gly Arg
            180                 185                 190

Val Leu Ala Gly Val Leu Ser Phe Ser Ser Arg Val Cys Thr Asp Ile
        195                 200                 205
```

Phe Lys Pro Pro Val Ala Thr Ala Val Ala Pro Tyr Val Ser Trp Ile
    210                 215                 220
Arg Lys Val Thr Gly Arg Ser Ala Ala Glu His Glu Gly Asp Ala Ala
225                 230                 235                 240
Gln Pro Ala Met Ala Gln Val Gln Leu Val Glu Ser Gly Gly Gly Val
            245                 250                 255
Val Gln Pro Gly Arg Ser Leu Arg Leu Ser Cys Ser Ser Ser Gly Phe
        260                 265                 270
Ile Phe Ser Asp Asn Tyr Met Tyr Trp Val Arg Gln Ala Pro Gly Lys
    275                 280                 285
Gly Leu Glu Trp Val Ala Thr Ile Ser Asp Gly Gly Ser Tyr Thr Tyr
290                 295                 300
Tyr Pro Asp Ser Val Lys Gly Arg Phe Thr Ile Ser Arg Asp Asn Ser
305                 310                 315                 320
Lys Asn Thr Leu Phe Leu Gln Met Asp Ser Leu Arg Pro Glu Asp Thr
            325                 330                 335
Gly Val Tyr Phe Cys Ala Arg Gly Tyr Tyr Arg Tyr Glu Gly Ala Met
        340                 345                 350
Asp Tyr Trp Gly Gln Gly Thr Pro Val Thr Val Ser Ser Gly Gly Gly
    355                 360                 365
Gly Ser Gly Gly Gly Gly Ser Gly Gly Gly Gly Ser Asp Ile Gln Leu
370                 375                 380
Thr Gln Ser Pro Ser Ser Leu Ser Ala Ser Val Gly Asp Arg Val Thr
385                 390                 395                 400
Ile Thr Cys Lys Ser Gln Ser Val Leu Tyr Ser Ser Asn Gln Lys
            405                 410                 415
Asn Tyr Leu Ala Trp Tyr Gln Gln Lys Pro Gly Lys Ala Pro Lys Leu
        420                 425                 430
Leu Ile Tyr Trp Ala Ser Thr Arg Glu Ser Gly Val Pro Ser Arg Phe
    435                 440                 445
Ser Gly Ser Gly Ser Gly Thr Asp Phe Thr Phe Thr Ile Ser Ser Leu
450                 455                 460
Gln Pro Glu Asp Ile Ala Thr Tyr Tyr Cys His Gln Tyr Leu Ser Ser
465                 470                 475                 480
Trp Thr Phe Gly Gln Gly Thr Lys Leu Glu Ile Lys
            485                 490

<210> SEQ ID NO 5
<211> LENGTH: 1464
<212> TYPE: DNA
<213> ORGANISM: Artificial Sequence
<220> FEATURE:
<223> OTHER INFORMATION: Gm-Ki4 (scFv)

<400> SEQUENCE: 5
atcatcgggg gccgggaggt gatcccccac tcgcgcccgt acatggcctc actgcagaga       60
aatggctccc acctgtgcgg gggtgtcctg gtgcacccaa agtgggtgct gacggctgcc      120
cactgcctgg cccagcggat ggcccagctg aggctggtgc tggggctcca caccctggac      180
agccccggtc tcaccttcca catcaaggca gccatccagc ccctcgcta caagcccgtc       240 cctgccctgg agaacgacct cgcgctgctt cagctggacg ggaaagtgaa gcccagccgg      300
accatccggc cgttggccct gcccagtaag cgccaggtgg tggcagcagg gactcggtgc      360
agcatggccg gctgggggct gacccaccag ggcgggcgcc tgtcccgggt gctgcgggag      420

-continued

```
ctggacctcc aagtgctgga cacccgcatg tgtaacaaca gccgcttctg gaacggcagc    480
ctctccccca gcatggtctg cctggcggcc gactccaagg accaggctcc ctgcaagggt    540
gactcgggcg ggcccctggt gtgtggcaaa ggccgggtgt tggccggagt cctgtccttc    600
agctccaggt ctgcactga catcttcaag cctcccgtgg ccaccgctgt ggcgccttac    660
gtgtcctgga tcaggaaggt caccggccga tcggccgctg agcacgaagg tgacgcggcc    720
cagccggcca tggcccaggt caagctgcag gagtcaggga ctgaactggc aaagcctggg    780
gccgcagtga agatgtcctg caaggcttct ggctacacct ttactgacta ctggatgcac    840
tgggttaaac agaggcctgg acagggtctg aatggattg gatacattaa tcctaacact    900
gcttatactg actacaatca gaaattcaag gacaaggcca cattgactgc agacaaatcc    960
tccagcacag cctacatgca actgcgcagc ctgacctctg aggattctgc agtctattac   1020
tgtgcaaaaa agacaactca gactacgtgg gggtttcctt tttggggcca agggaccacg   1080
gtcaccgtct cctcaggtgg aggcggttca ggcggaggtg gctctggcgg tggcggatcg   1140
gacattgtgc tgacccagtc tccaaaatcc atggccatgt cagtcggaga gggtcacc    1200
ttgagctgca aggccagtga gaatgtggat tcttttgttt cctggtatca acagaaacca   1260
ggccagtctc ctaaactgct gatatacggg gcctccaacc ggtacactgg ggtccccgat   1320
cgcttcgcag gcagtggatc tggaagagat ttcactctga ccatcagcag tgtgcaggct   1380
gaagaccttg cagattatca ctgtggacag aattacaggt atccgctcac gttcggtgct   1440
ggcaccaagc tggaaatcaa acgg                                          1464
```

<210> SEQ ID NO 6
<211> LENGTH: 488
<212> TYPE: PRT
<213> ORGANISM: Artificial Sequence
<220> FEATURE:
<223> OTHER INFORMATION: Gm-Ki4 (scFv)

<400> SEQUENCE: 6

```
Ile Ile Gly Gly Arg Glu Val Ile Pro His Ser Arg Pro Tyr Met Ala
1               5                   10                  15

Ser Leu Gln Arg Asn Gly Ser His Leu Cys Gly Gly Val Leu Val His
            20                  25                  30

Pro Lys Trp Val Leu Thr Ala Ala His Cys Leu Ala Gln Arg Met Ala
        35                  40                  45

Gln Leu Arg Leu Val Leu Gly Leu His Thr Leu Asp Ser Pro Gly Leu
    50                  55                  60

Thr Phe His Ile Lys Ala Ala Ile Gln His Pro Arg Tyr Lys Pro Val
65                  70                  75                  80

Pro Ala Leu Glu Asn Asp Leu Ala Leu Leu Gln Leu Asp Gly Lys Val
                85                  90                  95

Lys Pro Ser Arg Thr Ile Arg Pro Leu Ala Leu Pro Ser Lys Arg Gln
            100                 105                 110

Val Val Ala Ala Gly Thr Arg Cys Ser Met Ala Gly Trp Gly Leu Thr
        115                 120                 125

His Gln Gly Gly Arg Leu Ser Arg Val Leu Arg Glu Leu Asp Leu Gln
    130                 135                 140

Val Leu Asp Thr Arg Met Cys Asn Asn Ser Arg Phe Trp Asn Gly Ser
145                 150                 155                 160

Leu Ser Pro Ser Met Val Cys Leu Ala Ala Asp Ser Lys Asp Gln Ala
                165                 170                 175
```

-continued

Pro Cys Lys Gly Asp Ser Gly Gly Pro Leu Val Cys Gly Lys Gly Arg
              180                 185                 190

Val Leu Ala Gly Val Leu Ser Phe Ser Arg Val Cys Thr Asp Ile
         195                 200                 205

Phe Lys Pro Pro Val Ala Thr Ala Val Ala Pro Tyr Val Ser Trp Ile
        210                 215                 220

Arg Lys Val Thr Gly Arg Ser Ala Ala Glu His Glu Gly Asp Ala Ala
225                 230                 235                 240

Gln Pro Ala Met Ala Gln Val Lys Leu Gln Glu Ser Gly Thr Glu Leu
                245                 250                 255

Ala Lys Pro Gly Ala Ala Val Lys Met Ser Cys Lys Ala Ser Gly Tyr
            260                 265                 270

Thr Phe Thr Asp Tyr Trp Met His Trp Val Lys Gln Arg Pro Gly Gln
        275                 280                 285

Gly Leu Glu Trp Ile Gly Tyr Ile Asn Pro Asn Thr Ala Tyr Thr Asp
    290                 295                 300

Tyr Asn Gln Lys Phe Lys Asp Lys Ala Thr Leu Thr Ala Asp Lys Ser
305                 310                 315                 320

Ser Ser Thr Ala Tyr Met Gln Leu Arg Ser Leu Thr Ser Glu Asp Ser
                325                 330                 335

Ala Val Tyr Tyr Cys Ala Lys Lys Thr Thr Gln Thr Thr Trp Gly Phe
            340                 345                 350

Pro Phe Trp Gly Gln Gly Thr Thr Val Thr Val Ser Ser Gly Gly Gly
        355                 360                 365

Gly Ser Gly Gly Gly Gly Ser Gly Gly Gly Gly Ser Asp Ile Val Leu
    370                 375                 380

Thr Gln Ser Pro Lys Ser Met Ala Met Ser Val Gly Glu Arg Val Thr
385                 390                 395                 400

Leu Ser Cys Lys Ala Ser Glu Asn Val Asp Ser Phe Val Ser Trp Tyr
                405                 410                 415

Gln Gln Lys Pro Gly Gln Ser Pro Lys Leu Leu Ile Tyr Gly Ala Ser
            420                 425                 430

Asn Arg Tyr Thr Gly Val Pro Asp Arg Phe Ala Gly Ser Gly Ser Gly
        435                 440                 445

Arg Asp Phe Thr Leu Thr Ile Ser Ser Val Gln Ala Glu Asp Leu Ala
450                 455                 460

Asp Tyr His Cys Gly Gln Asn Tyr Arg Tyr Pro Leu Thr Phe Gly Ala
465                 470                 475                 480

Gly Thr Lys Leu Glu Ile Lys Arg
                485

<210> SEQ ID NO 7
<211> LENGTH: 1464
<212> TYPE: DNA
<213> ORGANISM: Artificial Sequence
<220> FEATURE:
<223> OTHER INFORMATION: Gm-425 (scFv)

<400> SEQUENCE: 7
atcatcgggg gccgggaggt gatcccccac tcgcgcccgt acatggcctc actgcagaga     60
aatggctccc acctgtgcgg gggtgtcctg gtgcacccaa gtgggtgct gacggctgcc    120 cactgcctgg cccagcggat ggcccagctg aggctggtgc tggggctcca caccctggac    180
agccccggtc tcaccttcca catcaaggca gccatccagc ccctcgcta caagcccgtc    240 cctgccctgg agaacgacct cgcgctgctt cagctggacg ggaaagtgaa gcccagccgg    300

```
accatccggc cgttggccct gcccagtaag cgccaggtgg tggcagcagg gactcggtgc   360
agcatggccg gctgggggct gacccaccag ggcgggcgcc tgtcccgggt gctgcgggag   420
ctggacctcc aagtgctgga cacccgcatg tgtaacaaca gccgcttctg aacggcagc    480
ctctccccca gcatggtctg cctggcggcc gactccaagg accaggctcc ctgcaagggt   540
gactcgggcg ggcccctggt gtgtggcaaa ggccgggtgt tggccggagt cctgtccttc   600
agctccaggt ctgcactga catcttcaag cctcccgtgg ccaccgctgt ggcgccttac    660
gtgtcctgga tcaggaaggt caccggccga tcggccgctg agcacgaagg tgacgcggcc   720
cagccggcca tggcgcaggt gcaactgcag cagtctgggg ctgaactggt gaagcctggg   780
gcttcagtga agttgtcctg caaggcttcc ggctacacct tcaccagcca ctggatgcac   840
tgggtgaagc agaggcctgg acaaggcctt gagtggatcg agagtttaa tcccagcaac    900
ggccgtacta actacaatga aaattcaag agcaaggcca cactgactgt agacaaatcc    960
tccagcacag cctacatgca actcagcagc ctgacatctg aggactctgc ggtctattac   1020
tgtgccagtc gggactatga ttacgacgga cggtactttg actactgggg ccaagggacc   1080
acggtcaccg tctcctcagg tggcggtggc tcgggcggtg gtgggtcggg tggcggcgga   1140
tctgacatcg agctcaccca gtctccagca atcatgtctg catctccagg ggagaaggtc   1200
actatgacct gcagtgccag ctcaagtgta acttacatgt attggtacca gcagaagcca   1260
ggatcctccc ccagactcct gatttatgac acatccaacc tggcttctgg agtccctgtt   1320
cgtttcagtg gcagtgggtc tgggacctct tactctctca caatcagccg aatggaggct   1380
gaagatgctg ccacttatta ctgccagcag tggagtagtc acatattcac gttcggctcg   1440
gggacagaac tcgagatcaa acgg                                          1464
```

<210> SEQ ID NO 8
<211> LENGTH: 488
<212> TYPE: PRT
<213> ORGANISM: Artificial Sequence
<220> FEATURE:
<223> OTHER INFORMATION: Gm-425 (scFv)

<400> SEQUENCE: 8

```
Ile Ile Gly Gly Arg Glu Val Ile Pro His Ser Arg Pro Tyr Met Ala
1               5                   10                  15

Ser Leu Gln Arg Asn Gly Ser His Leu Cys Gly Gly Val Leu Val His
                20                  25                  30

Pro Lys Trp Val Leu Thr Ala Ala His Cys Leu Ala Gln Arg Met Ala
            35                  40                  45

Gln Leu Arg Leu Val Leu Gly Leu His Thr Leu Asp Ser Pro Gly Leu
        50                  55                  60

Thr Phe His Ile Lys Ala Ala Ile Gln His Pro Arg Tyr Lys Pro Val
65                  70                  75                  80

Pro Ala Leu Glu Asn Asp Leu Ala Leu Leu Gln Leu Asp Gly Lys Val
                85                  90                  95

Lys Pro Ser Arg Thr Ile Arg Pro Leu Ala Leu Pro Ser Lys Arg Gln
            100                 105                 110

Val Val Ala Ala Gly Thr Arg Cys Ser Met Ala Gly Trp Gly Leu Thr
        115                 120                 125

His Gln Gly Gly Arg Leu Ser Arg Val Leu Arg Glu Leu Asp Leu Gln
    130                 135                 140

Val Leu Asp Thr Arg Met Cys Asn Asn Ser Arg Phe Trp Asn Gly Ser
```

| | | | | | | | | | | | | | | |
|---|---|---|---|---|---|---|---|---|---|---|---|---|---|---|
| | | 145 | | | 150 | | | | 155 | | | | 160 | |
| Leu | Ser | Pro | Ser | Met | Val | Cys | Leu | Ala | Ala | Asp | Ser | Lys | Asp | Gln | Ala |
| | | | | 165 | | | | 170 | | | | 175 | | |
| Pro | Cys | Lys | Gly | Asp | Ser | Gly | Gly | Pro | Leu | Val | Cys | Gly | Lys | Gly | Arg |
| | | | 180 | | | | 185 | | | | 190 | | | |
| Val | Leu | Ala | Gly | Val | Leu | Ser | Phe | Ser | Ser | Arg | Val | Cys | Thr | Asp | Ile |
| | | 195 | | | | 200 | | | | 205 | | | | |
| Phe | Lys | Pro | Pro | Val | Ala | Thr | Ala | Val | Ala | Pro | Tyr | Val | Ser | Trp | Ile |
| | 210 | | | | 215 | | | | 220 | | | | | |
| Arg | Lys | Val | Thr | Gly | Arg | Ser | Ala | Ala | Glu | His | Glu | Gly | Asp | Ala | Ala |
| 225 | | | | 230 | | | | 235 | | | | 240 | | |
| Gln | Pro | Ala | Met | Ala | Gln | Val | Gln | Leu | Gln | Gln | Ser | Gly | Ala | Glu | Leu |
| | | | 245 | | | | 250 | | | | 255 | | | |
| Val | Lys | Pro | Gly | Ala | Ser | Val | Lys | Leu | Ser | Cys | Lys | Ala | Ser | Gly | Tyr |
| | | 260 | | | | 265 | | | | 270 | | | | |
| Thr | Phe | Thr | Ser | His | Trp | Met | His | Trp | Val | Lys | Gln | Arg | Ala | Gly | Gln |
| | 275 | | | | 280 | | | | 285 | | | | | |
| Gly | Leu | Glu | Trp | Ile | Gly | Glu | Phe | Asn | Pro | Ser | Asn | Gly | Arg | Thr | Asn |
| 290 | | | | 295 | | | | 300 | | | | | | |
| Tyr | Asn | Glu | Lys | Phe | Lys | Ser | Lys | Ala | Thr | Leu | Thr | Val | Asp | Lys | Ser |
| 305 | | | 310 | | | | 315 | | | | 320 | | | |
| Ser | Ser | Thr | Ala | Tyr | Met | Gln | Leu | Ser | Ser | Leu | Thr | Ser | Glu | Asp | Ser |
| | | | 325 | | | | 330 | | | | 335 | | | |
| Ala | Val | Tyr | Tyr | Cys | Ala | Ser | Arg | Asp | Tyr | Asp | Tyr | Asp | Gly | Arg | Tyr |
| | | 340 | | | | 345 | | | | 350 | | | | |
| Phe | Asp | Tyr | Trp | Gly | Gln | Gly | Thr | Thr | Val | Thr | Val | Ser | Ser | Gly | Gly |
| | 355 | | | | 360 | | | | 365 | | | | | |
| Gly | Gly | Ser | Gly | Gly | Gly | Gly | Ser | Gly | Gly | Gly | Gly | Ser | Asp | Ile | Glu |
| | 370 | | | | 375 | | | | 380 | | | | | |
| Leu | Thr | Gln | Ser | Pro | Ala | Ile | Met | Ser | Ala | Ser | Pro | Gly | Glu | Lys | Val |
| 385 | | | | 390 | | | | 395 | | | | 400 | | |
| Thr | Met | Thr | Cys | Ser | Ala | Ser | Ser | Ser | Val | Thr | Tyr | Met | Tyr | Trp | Tyr |
| | | | 405 | | | | 410 | | | | 415 | | | |
| Gln | Gln | Lys | Pro | Gly | Ser | Ser | Pro | Arg | Leu | Leu | Ile | Tyr | Asp | Thr | Ser |
| | | 420 | | | | 425 | | | | 430 | | | | |
| Asn | Leu | Ala | Ser | Gly | Val | Pro | Val | Arg | Phe | Ser | Gly | Ser | Gly | Ser | Gly |
| | 435 | | | | 440 | | | | 445 | | | | | |
| Thr | Ser | Tyr | Ser | Leu | Thr | Ile | Ser | Arg | Met | Glu | Ala | Glu | Asp | Ala | Ala |
| | 450 | | | | 455 | | | | 460 | | | | | |
| Thr | Tyr | Tyr | Cys | Gln | Gln | Trp | Ser | Ser | His | Ile | Phe | Thr | Phe | Gly | Ser |
| 465 | | | | 470 | | | | 475 | | | | 480 | | |
| Gly | Thr | Glu | Leu | Glu | Ile | Lys | Arg | | | | | | | | |
| | | | | 485 | | | | | | | | | | | |

<210> SEQ ID NO 9
<211> LENGTH: 1446
<212> TYPE: DNA
<213> ORGANISM: Artificial Sequence
<220> FEATURE:
<223> OTHER INFORMATION: Gm-RFT5 (scFv)

<400> SEQUENCE: 9

```
atcatcgggg gccgggaggt gatcccccac tcgcgcccgt acatggcctc actgcagaga    60
aatggctccc acctgtgcgg gggtgtcctg gtgcacccaa gtgggtgct gacggctgcc    120
```

```
cactgcctgg cccagcggat ggcccagctg aggctggtgc tggggctcca caccctggac    180
agccccggtc tcaccttcca catcaaggca gccatccagc accctcgcta caagcccgtc    240
cctgccctgg agaacgacct cgcgctgctt cagctggacg ggaaagtgaa gcccagccgg    300
accatccggc cgttggccct gcccagtaag cgccaggtgg tggcagcagg gactcggtgc    360
agcatggccg gctggggct gacccaccag ggcgggcgcc tgtcccgggt gctgcgggag    420
ctggacctcc aagtgctgga cacccgcatg tgtaacaaca ccgcttctg gaacggcagc    480 ctctccccca gcatggtctg cctggcggcc gactccaagg accaggctcc ctgcaagggt    540
gactcgggcg ggcccctggt gtgtggcaaa ggcgggtgt tggccggagt cctgtccttc    600
agctccaggg tctgcactga catcttcaag cctcccgtgg ccaccgctgt ggcgccttac    660
gtgtcctgga tcaggaaggt caccggccga tcggccgctg agcacgaagg tgacgcggcc    720
cagccggccc aggtgaagct ggaggagtca gggactgtgc tggcaaggcc tgggcttcc    780 gtgaagatgt cctgcaaggc ttctggctac aggtttacca actactgat gcactgggta    840 aaacagaggc ctggacaggg tctagaatgg attggtgtta tttatcctgg aaatagtgat    900
actagctaca accagaagtt caagggcaag gccaaactga ctgcagtcac atccgccagc    960
actgcctaca tggagctcag cagcctgaca aatgaggact ctgcggtcta ttactgtaca    1020
agagagggag aaggctctga ctactggggc caagggacca cggtcaccgt ctcctcaggt    1080
ggaggcggtt caggcggagg tggctctggc ggtggcggat cgcaaattgt ctcacccag    1140 tctccagcaa ccatggctgc atctcccggg gagaagatca ctatcacctg cagtgccagc    1200
tcaagtataa gttccaatta cttgcattgg tatcagcaga agccaggatt ctcccctaaa    1260
ctcttgattt ataggacttc caatctggct tctggagtcc cagctcgctt cagtggcagt    1320
gggtctggga cctcttactc tctcacaatt ggcaccatgg aggctgaaga tgttgccact    1380
tactactgcc agcagggtag tagtataccg tacacgttcg gagggggac caagctggag    1440 ctcaaa                                                              1446
```

<210> SEQ ID NO 10
<211> LENGTH: 487
<212> TYPE: PRT
<213> ORGANISM: Artificial Sequence
<220> FEATURE:
<223> OTHER INFORMATION: Gm-RFT5 (scFv)

<400> SEQUENCE: 10

```
Ile Ile Gly Gly Arg Glu Val Ile Pro His Ser Arg Pro Tyr Met Ala
1               5                   10                  15

Ser Leu Gln Arg Asn Gly Ser His Leu Cys Gly Gly Val Leu Val His
                20                  25                  30

Pro Lys Trp Val Leu Thr Ala Ala His Cys Leu Ala Gln Arg Met Ala
            35                  40                  45

Gln Leu Arg Leu Val Leu Gly Leu His Thr Leu Asp Ser Pro Gly Leu
        50                  55                  60

Thr Phe His Ile Lys Ala Ala Ile Gln His Pro Arg Tyr Lys Pro Val
65                  70                  75                  80

Pro Ala Leu Glu Asn Asp Leu Ala Leu Leu Gln Leu Asp Gly Lys Val
                85                  90                  95

Lys Pro Ser Arg Thr Ile Arg Pro Leu Ala Leu Pro Ser Lys Arg Gln
                100                 105                 110

Val Val Ala Ala Gly Thr Arg Cys Ser Met Ala Gly Trp Gly Leu Thr
            115                 120                 125
```

-continued

```
His Gln Gly Gly Arg Leu Ser Arg Val Leu Arg Glu Leu Asp Leu Gln
        130                 135                 140

Val Leu Asp Thr Arg Met Cys Asn Asn Ser Arg Phe Trp Asn Gly Ser
145                 150                 155                 160

Leu Ser Pro Ser Met Val Cys Leu Ala Ala Asp Ser Lys Asp Gln Ala
                165                 170                 175

Pro Cys Lys Gly Asp Ser Gly Gly Pro Leu Val Cys Gly Lys Gly Arg
                180                 185                 190

Val Leu Ala Gly Val Leu Ser Phe Ser Ser Arg Val Cys Thr Asp Ile
            195                 200                 205

Phe Lys Pro Pro Val Ala Thr Ala Val Ala Pro Tyr Val Ser Trp Ile
        210                 215                 220

Arg Lys Val Thr Gly Arg Ser Ala Ala Glu His Glu Gly Asp Ala Ala
225                 230                 235                 240

Gln Pro Ala Gln Val Lys Leu Glu Glu Ser Gly Thr Val Leu Ala Arg
                245                 250                 255

Pro Gly Ala Ser Val Lys Met Ser Cys Lys Ala Ser Gly Tyr Arg Phe
                260                 265                 270

Thr Asn Tyr Trp Met His Trp Val Lys Gln Arg Pro Gly Gln Gly Leu
            275                 280                 285

Glu Trp Ile Gly Val Ile Tyr Pro Gly Asn Ser Asp Thr Ser Tyr Asn
        290                 295                 300

Gln Lys Phe Lys Gly Lys Ala Lys Leu Thr Ala Val Thr Ser Ala Ser
305                 310                 315                 320

Thr Ala Tyr Met Glu Leu Ser Ser Leu Thr Asn Glu Asp Ser Ala Val
                325                 330                 335

Tyr Tyr Cys Thr Arg Glu Gly Glu Gly Ser Asp Tyr Trp Gly Gln Gly
                340                 345                 350

Thr Thr Val Thr Val Ser Ser Gly Gly Gly Ser Gly Gly Gly Gly
            355                 360                 365

Ser Gly Gly Gly Gly Ser Gln Ile Val Leu Thr Gln Ser Pro Ala Thr
370                 375                 380

Met Ala Ala Ser Pro Gly Glu Lys Ile Thr Ile Thr Cys Ser Ala Ser
385                 390                 395                 400

Ser Ser Ile Ser Ser Asn Tyr Leu His Trp Tyr Gln Gln Lys Pro Gly
                405                 410                 415

Phe Ser Pro Lys Leu Leu Ile Tyr Arg Thr Ser Asn Leu Ala Ser Gly
                420                 425                 430

Val Pro Ala Arg Phe Ser Gly Ser Gly Ser Gly Thr Ser Tyr Ser Leu
            435                 440                 445

Thr Ile Gly Thr Met Glu Ala Glu Asp Val Ala Thr Tyr Tyr Cys Gln
        450                 455                 460

Gln Gly Ser Ser Ile Pro Tyr Thr Phe Gly Gly Gly Thr Lys Leu Glu
465                 470                 475                 480

Leu Lys Ala Ala Ala Gly Pro
                485
```